US008088388B2

(12) United States Patent
Sokoll

(10) Patent No.: US 8,088,388 B2
(45) Date of Patent: Jan. 3, 2012

(54) STABILIZED SYNTHETIC IMMUNOGEN DELIVERY SYSTEM

(75) Inventor: Kenneth K. Sokoll, Stony Brook, NY (US)

(73) Assignee: United Biomedical, Inc., Happauge, NY (US)

(*) Notice: Subject to any disclaimer, the term of this patent is extended or adjusted under 35 U.S.C. 154(b) by 1258 days.

(21) Appl. No.: 10/076,674

(22) Filed: Feb. 14, 2002

(65) Prior Publication Data

US 2003/0165478 A1 Sep. 4, 2003

(51) Int. Cl.

| | |
|---|---|
| *A61K 38/00* | (2006.01) |
| *A61K 47/00* | (2006.01) |
| *A61K 45/00* | (2006.01) |
| *A61K 31/70* | (2006.01) |
| *A61K 39/00* | (2006.01) |
| *A61K 39/38* | (2006.01) |
| *A61K 9/50* | (2006.01) |
| *A61K 38/16* | (2006.01) |
| *A01N 43/04* | (2006.01) |
| *A01N 37/18* | (2006.01) |

(52) U.S. Cl. ............ 424/185.1; 514/44 R; 514/2; 514/8; 424/184.1; 424/499; 424/278.1

(58) Field of Classification Search ............. 435/5, 91.1; 930/10; 424/1.45, 1.57, 1.65, 1.69, 1.73, 424/184.1, 185.1, 192.1, 193.1, 278.1
See application file for complete search history.

(56) References Cited

U.S. PATENT DOCUMENTS

| | | | | |
|---|---|---|---|---|
| 4,938,763 | A | 7/1990 | Dunn et al. | |
| 5,126,141 | A | 6/1992 | Henry | |
| 5,135,751 | A | 8/1992 | Henry | |
| 5,149,543 | A | 9/1992 | Cohen et al. | |
| 5,562,909 | A | 10/1996 | Allcock et al. | |
| 5,656,611 | A | 8/1997 | Kabanov et al. | |
| 5,700,459 | A | 12/1997 | Krone et al. | |
| 5,702,716 | A | 12/1997 | Dunn et al. | |
| 5,759,551 | A | 6/1998 | Ladd et al. | |
| 5,763,160 | A | 6/1998 | Wang | |
| 6,025,468 | A | 2/2000 | Wang | |
| 6,090,388 | A | 7/2000 | Wang | |
| 6,107,021 | A | 8/2000 | Wang et al. | |
| 6,194,388 | B1 | 2/2001 | Kreig et al. | |
| 6,207,646 | B1 | 3/2001 | Kreig et al. | |
| 6,312,731 | B1 | 11/2001 | Staas et al. | |
| 6,471,996 | B1 | 10/2002 | Sokoll et al. | |
| 6,573,238 | B2 | 6/2003 | Shirley et al. | |
| 6,623,764 | B1 | 9/2003 | Sokoll et al. | |
| 6,780,969 | B2 * | 8/2004 | Wang | 530/324 |
| 6,902,743 | B1 | 6/2005 | Setterstrom et al. | |
| 7,488,490 | B2 | 2/2009 | Davis et al. | |
| 2003/0026801 | A1 | 2/2003 | Weiner et al. | |
| 2003/0027979 | A1 * | 2/2003 | Wang | 530/317 |
| 2003/0055014 | A1 | 3/2003 | Bratzler | |
| 2003/0068325 | A1 * | 4/2003 | Wang | 424/185.1 |
| 2003/0165478 | A1 | 9/2003 | Sokoll | |
| 2004/0009897 | A1 * | 1/2004 | Sokoll | 514/7 |
| 2004/0185055 | A1 | 9/2004 | Glenn et al. | |
| 2004/0202680 | A1 | 10/2004 | O'Hagan | |
| 2005/0059619 | A1 | 3/2005 | Krieg et al. | |
| 2005/0079185 | A1 | 4/2005 | Parisot et al. | |
| 2005/0163745 | A1 | 7/2005 | Sokoll et al. | |
| 2005/0191319 | A1 | 9/2005 | O'Hagan et al. | |
| 2005/0208143 | A1 | 9/2005 | O'Hagan et al. | |
| 2005/0250726 | A1 | 11/2005 | Krieg et al. | |
| 2006/0002959 | A1 | 1/2006 | Glenn et al. | |

FOREIGN PATENT DOCUMENTS

| | | |
|---|---|---|
| CA | 2396884 | 8/2001 |
| WO | WO 91/04052 | 4/1991 |
| WO | WO 93/01286 | 1/1993 |
| WO | WO 94/25060 | * 11/1994 |
| WO | WO 9425060 | * 11/1994 |
| WO | WO 99/52549 | 10/1999 |
| WO | WO 99/66950 | 12/1999 |
| WO | WO 99/66957 | 12/1999 |
| WO | WO 99/67293 | 12/1999 |
| WO | WO01/22972 | * 4/2001 |
| WO | WO 0122972 | * 4/2001 |
| WO | WO 01/93903 | 12/2001 |
| WO | WO 01/97843 | 12/2001 |
| WO | WO 03/068169 | 8/2003 |

OTHER PUBLICATIONS

Result No. 1 of "rng" Sequence Search Summary.*
Result No. 1 of "rag" Sequence Search Summary.*
Result No. 1 of the rag search summary page.*
Result No. 1 of the mg search summary page.*
Morris et al. A novel potent strategy for gene delivery using a single peptide vector as a carrier. Nucleic Acid Research, 1999, vol. 27, No. 17, 3510-3517.*
Aguado MT, et al., *Immunobiol*, 1992, 184:113-125.
Aguiar JC, et al. *Vaccine*, 2002, 20:275-280.
Akasaka T, et al., *Bioconjugate Chem.*, 2001, 12:776-785.
Ballico M, et al., *Bioconjug Chem*, 2001, 12:719-725. Bjellqvist B, et al., *Electrophoresis*, 1993, 14:1023-1031.
Chu RS, et al., *J Exp Med*, 1997, 186:1623-1631.
Cox JC, et al. *Vaccine*, 1997, 15:248-256.
DesNoyer JR, et al., *J Controlled Release*, 2001, 70:285-294.
Eldridge JH, et al., *Mol Immunol*, 1991, 28:287-297.
Forbes RT, et al., *J Pharm Sci*, 1998, 87:13161321.
Graham PD, et al., *J Controlled Release*, 1999, 58:233-245.
Hanson CV, et al., *J. Clin Microbiol*, 1990, 28:2030-2034.
Higaki M, et al., *Vaccine*, 1998, 16:741-745.
Hilbert AK, et al., Vaccine, 1999, 17:1065-1073.
Ikada Y, et al., *J Bioactive Compat Polym*, 1986, 1:32-46.

(Continued)

*Primary Examiner* — N. M Minnifield
(74) *Attorney, Agent, or Firm* — Locke Lord LLP

(57) ABSTRACT

The present invention provides an immunostimulatory complex specifically adapted to act as adjuvant and as a peptide immunogen stabilizer. The immunostimulatory complex comprises a CpG oligonucleotide and a biologically active peptide immunogen. The immunostimulatory complex is particulate and can efficiently present peptide immunogens to the cells of the immune system to produce an immune response. The immunostimulatory complex may be formulated as a suspension for parenteral administration. The immunostimulatory complex may also be formulated in the form of w/o-emulsions or in-situ gelling polymers for the efficient delivery of immunogens to the cells of the immune system of a subject following parenteral administration, to produce an immune response.

26 Claims, 12 Drawing Sheets

OTHER PUBLICATIONS

Jepson MA, et al. *J Drug Targeting*, 1993, 1:245-249.
Jones TR, et al., *Vaccine*, 1999, 17:3065-3071.
Kabanov AV, et al., *Bioconjug Chem*, 1995, 6:7-20.
Klinman DM, et al., *Vaccine*,1999, 17:19-25.
Klinman DM, et al., *Infect Immun*, 1999, 67:5658-5663.
Kreuter J, et al. *Vaccine*, 1986, 4:125-129.
Krieg AM, et al., *Nature* 1995, 374:546-549.
LiCalsi C, et al., *Vaccine*, 1999, 17:1796-1803.
MacDonald RC, et al., *Biochim Biophys Acta*, 1991, 1061:297-303.
Manning MC, et al. Pharmaceutical Research, 1989, 6:903-918.
Mascotti DP, et al., *Proc Nat Acad Sci*, USA, 1990, 87:3142-3146.
Matsuo K, et al. *Vaccine*, 2000, 18:1344-1350.
McCluskie MJ, et al., *Vaccine*, 2000, 18:231-237.
Moldoveanu Z, et al., *J Infect Dis*, 1993, 167:84-90.
Monfardini C, et al., Bioconjugate Chem., 1998, 9:418-450.
Nagel KM, et al., *Pharmacotherapy*, 1993, 13:177-188.
Overcashier DE, et al., *J Pharm Sci*, 1999, 88:688-695.
Papisov IM, et al., *Advances in Polymer Science*, 1988, 90, 1988,139-177.
Park TG, et al., *J Controlled Release*, 1995, 33:211-222.
Powell MF, et al., *Pharmaceutical Biotechnology*, vol. 6, Plenum Press, New York, 1995.
Roberts MJ, et al., J Pharm Sci, 1998, 87:1440-1445.
Romera SA, et al., *Vaccine*, 2001, 19:132-141.
Scharton-Kersten T, et al. *Infect Immun*, 2000, 68:5306-5313.
Shen F, et al., *Vaccine*, 1999, 17:3039-3049.
Suharyono, et al. *Lancet*, 1992, 340:689-694.
Visscher GE, et al., *J Biomed Mater Res*, 1985, 19:349-365.
Wang CY, et al., *Proc. Nat. Acad. Sci.*, USA, 1999, 96:10367-10372.
Weeratna RD, et al., *Vaccine*, 2000, 18:1755-1762.
Wright JC, et al., *J Controlled Release*, 2001, 75:1-10.
European Search Report for corresponding European Patent Application No. 037091345-1222 (PCT/US03/04711), dated Apr. 1, 2008.
Shieh et al., "Enhancement of the immunity to foot-and-mouth disease virus by DNA priming and protein boosting immunization", *Vaccine*, (2001); 19:4002-4010.
Jones et al., "Synthetic oligodeoxynucleotides containing CpG motifs enhance immunogenicity of a peptide malaria vaccine in Aotus monkeys", *Vaccine*, (1999); 17:3065-3071.
Stern, B. et al, "Vaccination with Tumor Peptide in CpG Adjuvant Protects Via IFN—Dependent CD4 Cell Immunity" *J. Immunology* (2002), 168:6099-6105.
Maurer, TA, et al, "CpG-DNA aided cross-presentation of soluble antigens by dendritic cells." *Eur. J. Immunol.* (2002), 32:2356-2364.
Singh, M. et al, "Recent advances in vaccine adjuvants" *Pharmaceutical Research*, (2002), 19(6):715-728.
O'Hagen, DT, et al, "Recent developments in adjuvants for vaccines against infectious diseases" *Biomolecular Engineering* (2001), 18:69-85.
Singh, M, et al, "Recent advances in veterinary vaccine adjuvants" *International J. Parasitology*, (2003), 33:469-478.
O'Hagen, DT, "Recent Developments in Vaccine Delivery Systems" *Current Drug Targets—Infectious Disorders* (2001), 1:273-286.
Dittmer, U, et al, "Treatment of infectious diseases with immunostimulatory oligodeoxynucleotides containing CpG motifs" *Current Opinion in Microbiology*, (2003), 6:472-477.
Yoshinaga, T, et al, "DNA and its cationic lipid complexes induce CpG motif-dependent activation of murine dendritic cells" *Immunology*, (2006), 120:295-302.
Riedl, P, et al, "Peptides containing antigenic and cationic domains have enhanced, multivalent immunogenicity when bound to DNA vaccines" *J. Mol. Med.*, (2004), 82:144-152.
Diminsky, D, et al, "Physical, chemical and immunological stability of CHO-derived hepatitis B surface antigen (HBsAg) particles" *Vaccine*, (2000), 18:3-17.
Morita, T, et al, "Preparation of gelatin microparticles by co-lyophilization with poly(ethylene glycol): characterization and application to entrapment into biodegradable microspheres" *International J. Pharmaceutics* (2001), 219:127-137.
Ivins, B, et al, "Experimental anthrax vaccines: efficacy of adjuvants combined with protective antigen against an aerosol *Bacillus anthracis* spore challenge in guinea pigs" *Vaccines*, (1995), 13/18:1779-1784.
Gupta, RK, et al, "Determination of protein loading in biodegradable polymer microspheres containing tetanus toxoid" *Vaccine*, (1997), 15(6/7):672-678.
Hakim, I, et al, "A nine-amino acid peptide from IL-1beta augments antitumor immune responses induced by protein and DNA vaccines" *J. Immunol.*, (1996), 157:5503-5511.
Zeng, XY, et al, "Effects of active immunization against GnRH on serum LH, inhibin A, sexual development and growth rate in Chinese female pigs" *Theriogenology* (2002), 58:1315-1326.
Proietti, E. et al, "Type I IFN as a natural adjuvant for a protective immune response: lessons from the influenza Vaccine Model" *J. Immunol.*, (2002), 169:375-383.
"Foot and Mouth Disease" in OIE Manual of Standards for Diagnostic Tests and Vaccines, publisher: Springer Netherlands, Ch. 2.1.1, (1997).
Nesburn, AB, et al, "Local and systemic B cell and Th1 responses induced following ocular mucosal delivery of multiple epitopes of herpes simplex virus type 1 glycoprotein D together with cytosine-phosphate-guanine adjuvant" *Vaccine*, (2005), 23:873-883.
Examiner's Requisition as issued in the related Canadian Patent Application No. 2,475, 102; dated Jun. 3, 2010.
Oxenius, A., et al., "CpG-Containing oligonucleotides are efficient adjuvants for induction of protective antiviral immune responses with T-Cell peptide vaccines", *Journal of Virology*, 73(5): 4120-4126. (1999).

* cited by examiner

Schematic Of Complexation Process

LHRH Synthetic Immunogens:CpG1 Oligonucleotide Complexes Particle Size Distribution Vs. Relative Molar Charge Ratio

Schematic Of W/O Emulsion Process Via Homogenization Or Extrusion

Homogenized W/O Emulsion

LHRH Peptides : CpG1 Oligonucleotides (ratio 4:1)

Extruded W/O Emulsion

LHRH Peptides : CpG1 Oligonucleotides (ratio 4:1)

200x 5um

Schematic Of Polymer In-Situ Gel Process Via Reconstitution

(IgE Peptides/CpG1 Complexes + Homogenized W/O Emulsions)
3 immunizations (week 0, 3, 6), Bleeds (week 3, 5, 9,11,17)

(CD4 Peptides/CpG2 Complexes + Homogenized W/O Emulsions)
3 immunizations (week 0, 3, 6), Bleeds (week 3, 5, 9,11,17)

(IgE Peptides/CpG1 Complexes + Extruded W/O Emulsions)
3 immunizations (week 0, 3, 6), Bleeds (week 3, 5, 9,11,17)

(CD4 Peptides/CpG2 Complexes + Extruded W/O Emulsions)
3 immunizations (week 0, 3, 6), Bleeds (week 3, 5, 9,11,17)

(IgE Peptides/CpG1 Complexes + PLGA/DMSO Gels)
Single Dose Immunization, Bleeds (week 3, 6, 9,12)

(CD4 Peptides/CpG2 Complexes + PLGA/DMSO Gels)
Single Dose Immunization, Bleeds (week 3, 6, 9,12)

STABILIZED SYNTHETIC IMMUNOGEN DELIVERY SYSTEM

FIELD OF THE INVENTION

The present invention relates to a stabilized immunostimulatory complex and a method for preparing the stabilized immunostimulatory complex. More specifically, the present invention provides stabilized synthetic immunostimulatory complexes that are useful in vaccine delivery systems with improved immune responses in vivo. These immunostimulatory complexes are also useful for preparing vaccine formulations designed to function as a depot for controlled release of the immunostimulatory complex. The immunostimulatory complex may also be incorporated in formulations designed to target specific cell types to synergistically improve the quality of the immune responses elicited.

BACKGROUND OF THE INVENTION

Vaccines have been successfully employed for many years in prophylactic compositions for the prevention of infectious disease and more recently in therapeutic compositions for the treatment of cancers and non-infectious diseases.

Traditionally vaccines have been derived from attenuated or killed viral or bacterial pathogens and have proven to be very effective against diseases such as polio virus and *Bordetella pertussis*. In spite of these successes, there are growing concerns over the safety of such vaccines. This has led to the development of subunit vaccines derived from components of these pathogens or fully synthetic peptide immunogens.

Examples of subunit vaccines include Tetanus toxoid and hepatitis B surface antigen. These antigens are often poorly immunogenic and require adjuvants to improve the immune responses obtained. Well-characterized biologically active compounds such as synthetic peptides are preferred substrates for inducing biological responses, for safety and regulatory purposes. However, these immunogens are not optimal, and induce partial or negligible protective responses in animal models. The synthetic peptides require both stabilization and adjuvantation for the induction of an effective immune response in vivo.

Various methods have been employed to protect synthetic peptide immunogens against degradation in vitro and in vivo, mediated by various processes including chemical and physical pathways.[1] (The superscript numbers refers to publications which more fully describe the state of the art to which this invention pertains. The disclosures of these references are hereby incorporated by reference. The citation of each reference is found at the end of this section.)

Various methods have been employed to improve peptide solubility or protect a peptide against degradation in vivo.[2] These generally include simple procedures like modifying the salt concentration and/or the pH of the solution. Peptides have also been chemically modified by conjugation with water soluble compounds like polyethylene glycol (PEG) or polyethylene oxide (PEO) both to improve their aqueous solubility and circulation time in vivo.[3] It has been documented that adjuvants derived from PEG or PEO can down regulate the immune system.[4] Thus, PEG or PEO modified peptides would not be expected to function effectively as adjuvants. The addition of multiple lysines to add charge to a peptide can improve its aqueous solubility but does not generally result in improved immunogenicity.

The objective of these various strategies is to improve circulation time in vivo or minimize or eliminate immunogenicity problems associated with the physical conditions (e.g. salt, pH, temperature, buffer type) and/or chemical incompatibilities when peptides are employed in a vaccine formulation.

Polyether block copolymers, comprising polycationic polymers, were disclosed by Kabanov et al., U.S. Pat. No. 5,656,611[5] for stabilizing polynucleotides or oligonucleotides. The polyether block copolymer-polynucleotide complexes are employed to facilitate the transport of the polynucleotide across a cell membrane for improved biological activity. However, these polynucleotide-polyether block copolymers are not immunogenic and are not suitable as vaccines.

Allcock et al. U.S. Pat. No. 5,562,909[6] describes an immunoadjuvant derived from phosphazene polyelectrolytes. The immunoadjuvant was admixed directly with an antigen in solution and may be prepared as microparticles by spray drying a solution of the polymer and the antigen or by a process described by Cohen in U.S. Pat. No. 5,149,543.[7] Although, increased adjuvanticity was shown for these systems, there are difficulties in preparing the microparticular compositions due to the cumbersome mechanical processes employed, which would be difficult to scale up for commercial production. Furthermore, the stability of the polymer-antigen complex so formed is highly dependent on salt concentration and pH conditions.

A different approach is described in Moss et al. WO91/04052[8], wherein a solid vaccine composition is prepared from an antigen, which may be a peptide, a saponin and a polycationic adjuvant such as DEAE-dextran. Vaccines formulated from this combination provided improved longevity, making such combinations suitable for use as implants. However, the antigen must first be chemically conjugated to a carrier molecule and exhaustively purified. The purified antigen-carrier was then combined with a saponin and a polycationic adjuvant to provide a solid composition. This process provides no control over the physical properties, such as particle size, of the product.

Numerous adjuvants and/or depot-based parenteral, mucosal or transdermal delivery systems destined for use with human or veterinary vaccines have been developed to enhance the immune response. These include the use of mineral salts, water-in-oil (w/o)-emulsions, liposomes, polymeric microparticles, nanoparticles and gels/hydrogels.[9] A large number of clinical trials employing various (w/o)-emulsion compositions have been conducted.

In spite of this vast body of clinical research, typical parenteral formulations, administered subcutaneously or intramuscularly, are prepared with adjuvants derived from aluminum salts, such as aluminum phosphate or aluminum hydroxide. Alum salts are suitable and effective for many vaccines based on attenuated pathogens, killed pathogens and subunit antigens derived from biological agents. However, the aluminum-based adjuvants are often totally ineffective for synthetic peptide-based immunogens because of the large dose of peptide required and the need of much stronger adjuvantation. The combination of a large dose of immunogen with a weakly adjuvanting alum in a vaccine composition is not ideal as it can lead to immunogen tolerance and reactogenicity, i.e. undesired side reactions, such as swelling and redness at the site of injection.

Freund's complete adjuvant (FCA), a suspension of heat-killed *M. tuberculosis* mycobacteria in mineral oil containing a surfactant, has been recognized as one of the most powerful adjuvant. However, severe adverse reactions, ranging from minor irritation to lesions and sterile abscesses at the site of injection have been documented. Due to these adverse reactions, FCA has been banned from human and veterinary applications.

Thus, there is a clear need to develop adjuvants which are safe without the toxicological and/or reactogenic problems associated with alum or FCA and can effectively enhance immunogenicity and prolong the effectiveness of peptide immunogens to avoid the problem of tolerance associated with alum. It is also most desirable to develop compositions and methods which can both stabilize a peptide immunogen and adjuvant the immune responses in a single composition.

Jones et al.[10] have disclosed two specific CpG oligonucleotides that may be co-administered with a peptide-based malaria vaccine in Aotus monkeys to enhance immune responses. In the Jones study, the ionization point (IP) of the peptide used is 5.96 and has a theoretical zero charge.[11] By virtue of its amino acid composition, the peptide used would be effectively uncharged at physiological pH in the aqueous solvent selected. Thus, no complexation can take place with the two CpG oligomers. The resultant mixture when formulated in a w/o-emulsion is expected to be transiently adjuvanted. To achieve a useful level of immunogenicity, multiple injections and a large quantity of adjuvant would be required. Further, the long-term stability of such a composition is questionable. In fact, Jones et al. disclosed that it was necessary to employ a large dose of CpG oligonucleotide, 500 μg per injection. Furthermore, the methods, employed to prepare the w/o-emulsions, cannot be easily scaled up for commercial applications. It is to be noted that Jones et al. taught that different CpG oligomers are useful for different mammalian species. For example, a CpG oligomer, CpG ODN 1826 is mitogenic for mice and a lower primate, but not for chimpanzees or humans and the effect is not predictable.

Krieg et al., U.S. Pat. No. 6,194,388 B1[12] describes unmethylated CpG oligonucleotides particularly useful for therapeutic applications based on their ability to stimulate immune responses when mixed with an antigen. Krieg et al., U.S. Pat. No. 6,207,646 B1[13] further describes the use of unmethylated CpG oligonucleotides to redirect a Th2 response to a Th1 response. In both, the effectiveness of the CpG oligomers were shown by B-cell stimulation wherein B-cells were cultured with phosphorothioate modified CpG oligomers. There is no disclosure or suggestion on how the CpG oligomers can be used to provide a stabilized immunostimulatory complex or a vaccine.

Another area of intense interest and research has been focused on methods to formulate synthetic immunogens for alternate delivery routes, such as mucosally, transdermally, or orally. Mucosal immunity is mediated by the induction of secretory immunoglobulin (sIgA) found in external secretions (e.g. intestinal, bronchial or nasal washings). It is believed that transdermal or mucosal delivery of vaccines would be effective against a majority of pathogenic organisms which gain entry via mucosal surfaces. For example, an orally administered cholera vaccine has been shown to be far superior to the parenterally administered analog.[14]

Friede et al., WO99/52549[15] teaches that vaccine compositions intended for mucosal use can be derived from a combination of an antigen with a polyoxyethylene ether or polyoxyethylene ester as the primary adjuvant. It was suggested that the target antigen may be a synthetic peptide. Friede et al. also suggest the addition of CpG oligonucleotides into the vaccine composition to provide improved responses. They showed that a combination of a polyoxyethylene ether or polyoxyethylene ester with a CpG oligonucleotide can improve mucosal responses when co-administered with an antigen. However, the results showed lack of any adjuvanticity from the various mixtures of CpG ha oligonucleotides with antigen described.

Transdermally administered vaccines represent an area of recent interest. Ideally, devices, i.e., patches or needle-free jet injectors, can be employed to target the intradermal Langerhan cells, i.e., dendritic cells. These specialized cells are responsible for the effective processing and presentation of an immunogen and can be used to directly induce systemic humoral and cellular responses. In some cases, intramuscular immunization was achieved by transdermal methods.[16] For example, a recent paper described a diptheria vaccine administered as a patch. Systemic antibodies to diptheria toxoid were found for a variety of compositions when co-administered with adjuvants.[17]

Although the prior art has illustrated the potential of various vaccine formulations, there are a number of practical limitations for the development of synthetic peptide-based vaccine formulations for mucosal or transdermal delivery. These include:

1) immunogen degradation by mucosal fluids or secretions and/or proteolytic enzymes at the mucosal surface or within the intradermis;
2) negligible adsorption across the mucosal epithelium or through the intradermal layers; and
3) dilution of the immunogen to a concentration below that required to induce a suitable level of immune responses.

Few strategies exist which both stabilize and adjuvant a synthetic peptide-based immunogen in a single vaccine composition. Such a composition would be essential for the development of highly efficacious parenteral, mucosal or transdermal vaccines.

It is also desirable to prolong the duration of immunogenic responses in order to reduce the number of administrations required. This would result in improved compliance and reduce the overall cost for vaccination.

Various methods may be employed to adjuvant synthetic peptide-based immunogens, but normally a carrier or depot system is required for effective long-term immunogenic responses. Notable examples include adsorbing the immunogen onto a mineral salt or gel. For example, encapsulating a peptide immunogen within a polymeric matrix (monolithic matrix) or gel, or layering a polymeric material around a peptide immunogen (core-shell) may be an effective strategy. Or, an immunogen may be incorporated in a liposome or vesicular type of formulation, with the immunogen either embedded in the lipid matrix or physically entrapped in the internal aqueous phase. Another strategy may employ a mineral-based, vegetable-based or animal-based oil, with an aqueous solution of the immunogen in various proportions, to prepare a water-in-oil (w/o)-emulsion or a water-in-oil-in-water (w/o/w)-double emulsion[18].

Diverse particle sizes, morphologies, surface hydrophobicity and residual surface charge are possible formulation dependent variables for consideration. Control of these parameters is known to be important for the phagocytosis of micron-sized particulates via parenteral administration[19, 20] and for the uptake of particulates at specialized M-cells of the Peyers Patches within the intestinal tract[21, 22] for oral delivery. Similarly, these parameters have been shown to be important for access to the nasal-associated lymphoid tissue of the nasalpharyngeal tract, a target of intranasal delivery.[23, 24]

Krone et al., U.S. Pat. No. 5,700,459[25] describes the use of polyelectrolyte complexes in microparticulate form derived from polyacids and polybases, in which the complexing agent is a polymer. Various uses for these complexes, are described and include vaccine compositions comprising antigens or antigenic peptides. Some of the compositions are controlled release formulations employing potentially biodegradable materials. In one of the examples, a method of incorporating an antigen in polyelectrolyte complex microparticles is described. However, the mechanical process described for preparing microparticles by grinding the mixture of 100 μM size particles to about 1-4 μM, is cumbersome. This would not be easily scaled up for commercial production.

Eldridge et al.[26] developed polymeric biodegradable microspheres manufactured from poly-D,L-lactide-co-glycolide copolymers for the controlled release of an antigen in vivo. The polymers disclosed to be useful for encapsulating an antigen into microparticles include poly-D,L-lactide, polyglycolide, polycaprolactone, polyanhydrides, polyorthoesters and poly(α-hydroxybutyric acid).

Although the controlled release of an antigen was achieved in the prior art, difficulties were encountered when microparticles were manufactured by methods described. The methods described are difficult to scale-up. Moreover, the exposure of biological materials to organic solvents and mechanical processing can lead to denaturation and low to modest encapsulation efficiencies. Furthermore, hydrophilic antigens are inefficiently encapsulated in the processes described.

Henry, et al., U.S. Pat. Nos. 5,126,141 and 5,135,751[27, 28] described aqueous, thermally reversible gel compositions formed from a polyoxyalkylene polymer and an ionic polysaccharide for application to injured areas of the body to prevent adhesion. Rosenberg, et al., WO93/01286[29] described the use of the same type of polyoxyalkylene polymers for the local delivery of antisense oligonucleotides to surgically exposed surface of blood vessels for treatment of restenosis. Neither Henry et al. or Rosenberg et al. taught or suggest the use of a gel composition as a vaccine.

Dunn et al., U.S. Pat. Nos. 4,938,763 and 5,702,716[30, 31] describe polymeric compositions useful for the controlled release of biologically active materials. A biocompatible solvent was used to prepare solutions or suspensions of antigen for direct parenteral injection, whereupon in-situ gelling results in implant formation. Utility for a variety of antigens including small synthetic peptide-based immunogens was claimed. However, Dunn et al., U.S. Pat. No. 5,702,716[31], stated that the controlled release compositions require up to 15% by weight of a gel rate-retarding agent. The retarding agents were added to modulate the gelling rate and were needed for higher entrapment efficiencies for antigens which are easily extracted in vivo. As the solvent extraction is governed largely by diffusion, this presents more of a problem for small synthetic immunogens than for larger sub-unit or protein-based antigens.

Neither U.S. Pat. No. 4,938,763[30] nor U.S. Pat. No. 5,702,716[31] taught nor suggested synthetic peptide-based immunogen stabilized as an immunostimulatory complex suspended within a biocompatible solvent. Furthermore, neither U.S. Pat. No. 4,938,763[30] nor U.S. Pat. No. 5,702,716[31] taught nor suggested compositions which are self adjuvanting and can upregulate immune responses in both the priming and boosting phases.

It is an object of this invention to develop stable immunostimulatory complexes from synthetic peptide immunogens and stabilizing molecules, which possess self adjuvanting properties in vivo. It is a further object of the present invention to provide a simple method to stabilize a synthetic peptide immunogen in vitro and in vivo.

It is a still further object of the present invention to provide sustained or controlled release delivery vehicles compatible with these stabilized synthetic peptide-based immunostimulatory complexes.

It is a still further object of the invention to develop formulations using a combination of stabilized synthetic peptide-based immunostimulatory complexes and uncomplexed immunogens in a controlled release delivery system to achieve a synergistic enhancement of the immune responses.

REFERENCES CITED

1. Manning M C, et al. *Pharmaceutical Research,* 1989, 6:903-918.
2. Monfardini C, et al., *Bioconjugate Chem.,* 1998, 9:418-450.
3. Roberts M J, et al., *J Pharm Sci,* 1998, 87:1440-1445.
4. Hilbert A K, et al., *Vaccine,* 1999, 17:1065-1073.
5. Kabanov A V, et al., U.S. Pat. No. 5,656,611, 1997.
6. Allcock H R, et al., U.S. Pat. No. 5,562,909, 1996.
7. Cohen S, et al., U.S. Pat. No. 5,149,543, 1992.
8. Moss B A, et al., WO 91/04052, 1991.
9. Cox J C, et al. *Vaccine,* 1997, 15:248-256.
10. Jones T R, et al., *Vaccine,* 1999, 17:3065-3071.
11. Bjellqvist B, et al., *Electrophoresis,* 1993, 14:1023-1031.
12. Kreig A M, et al., U.S. Pat. No. 6,194,388 B1, 2001.
13. Kreig A M, et al., U.S. Pat. No. 6,207,646 B1, 2001.
14. Suharyono, et al. *Lancet,* 1992, 340:689-694.
15. Freide M, Hermand P., WO 99/52549, 1999.
16. Aguiar J C, et al. *Vaccine,* 2002, 20:275-280.
17. Scharton-Kersten T, et al. *Infect Immun,* 2000, 68:5306-5313.
18. Powell M F, et al., *Pharmaceutical Biotechnology,* Vol. 6, Plenum Press, New York, 1995.
19. Ikada Y, et al., *J Bioactive Compat Polym,* 1986, 1:32-46.
20. Kreuter J, et al. *Vaccine,* 1986, 4:125-129.
21. Jepson M A, et al. *J Drug Targeting,* 1993, 1:245-249.
22. Moldoveanu Z, et al., *J Infect Dis,* 1993, 167:84-90.
23. Matsuo K, et al. *Vaccine,* 2000, 18:1344-1350.
24. Higaki M, et al., *Vaccine,* 1998, 16:741-745.
25. Krone V, et al., U.S. Pat. No. 5,700,459, 1997.
26. Eldridge J H, et al., *Mol Immunol,* 1991, 28:287-297.
27. Henry R L, U.S. Pat. No. 5,126,141,1992.
28. Henry R L, U.S. Pat. No. 5,135,751, 1992.
29. Rosenberg R D, et al., WP 93/01286, 1993.
30. Dunn R L, et al., U.S. Pat. No. 4,938,763, 1990.
31. Dunn R L, et al., U.S. Pat. No. 5,702,716, 1997.
32. Papisov I M, et al., *Advances in Polymer Science,* 1988, 90, 1988, 139-177.
33. Chu R S, et al., *J Exp Med,* 1997, 186:1623-1631.
34. Akasaka T, et al., *Bioconjugate Chem.,* 2001, 12:776-785.
35. Ballico M, et al., *Bioconjug Chem,* 2001, 12:719-725.
36. Klinman D M, et al., *Vaccine,* 1999, 17:19-25.
37. Krieg A M, et al., *Nature* 1995, 374:546-549.
38. Klinman D M, et al., *Infect Immun,* 1999, 67:5658-5663.
39. Nagel K M, et al., *Pharmacotherapy,* 1993, 13:177-188.
40. Weeratna R D, et al., *Vaccine,* 2000, 18:1755-1762.
41. McCluskie M J, et al., *Vaccine,* 2000, 18:231-237.
42. LiCalsi C, et al., *Vaccine,* 1999, 17:1796-1803.
43. Romera S A, et al., *Vaccine,* 2001, 19:132-141.
44. Wright J C, et al., *J Controlled Release,* 2001, 75:1-10.
45. Graham P D, et al., *J Controlled Release,* 1999, 58:233-245.
46. DesNoyer J R, et al., *J Controlled Release,* 2001, 70:285-294.
47. Aguado M T, et al., *Immunobiol,* 1992, 184:113-125.
48. Visscher G E, et al., *J Biomed Mater Res,* 1985, 19:349-365.
49. Forbes R T, et al., *J Pharm Sci,* 1998, 87:13161321.
50. Overcashier D E, et al., *J Pharm Sci,* 1999, 88:688-695.
51. Wang C Y, et al., WO 99/67293, 1999.

52. Wang C Y, U.S. Pat. No. 5,763,160, 1998.
53. Wang C Y, U.S. Pat. No. 6,090,388, 2000.
54. Ladd A E, et al., U.S. Pat. No. 5,759,551, 1998.
55. Wang C Y, U.S. Pat. No. 6,025,468, 2000.
56. Wang C Y, U.S. Ser. No. 09/865,294, 2001.
57. Wang C Y, et al., U.S. Pat. No. 6,107,021, 2000.
58. Wang C Y, U.S. Ser. No. 09/747,802, 2001.
59. Wang C Y, WO 99/66957, 1999.
60. Wang C Y, WO 99/66950, 1999.
61. Mascotti D P, et al., *Proc Nat Acad Sci,* USA, 1990, 87:3142-3146.
62. Kabanov A V, et al., *Bioconjug Chem,* 1995, 6:7-20.
63. MacDonald R C, et al., *Biochim Biophys Acta,* 1991, 1061:297-303.
64. Shen F, et al., *Vaccine,* 1999, 17:3039-3049.
65. Wang C Y, et al., *Proc. Nat. Acad. Sci*., USA, 1999, 96:10367-10372.
66. Hanson C V, et al., *J. Clin Microbiol,* 1990, 28:2030-2034.
67. Park T G, et al., *J Controlled Release,* 1995, 33:211-222.
68. Wright J C, et al. *J Controlled Release,* 2001, 75: 1-10.

SUMMARY OF THE INVENTION

The present invention is directed to a stabilized immunostimulatory complex comprising a cationic petide and anionic molecule or oligonucleotide or polynucleotide and a method for stabilizing a cationic peptide by complexation with an anionic molecule or oligonucleotide or polynucleotide via electrostatic association. The stabilized immunostimulatory complex may be incorporated into a pharmaceutical composition as an immunogen delivery system.

A "cationic peptide" as described herein refers to a peptide which is positively charged at a pH in the range of 5.0 to 8.0. The net charge on the peptide or peptide cocktails is calculated by assigning a +1 charge for each lysine (K), arginine (R) or histidine (H), a −1 charge for each aspartic acid (D) or glutamic acid (E) and a charge of 0 for the other amino acid within the sequence. The charge contributions from the N-terminal amine (+1) and C-terminal carboxylate (−1) end groups of each peptide effectively cancel each other when unsubstituted. The charges are summed for each peptide and expressed as the net average charge. A suitable peptide immunogen has a net average positive charge of +1. Preferably, the peptide immunogen has a net positive charge in the range that is larger than +2.

The peptide immunogens comprise B-cell epitopes and Th epitopes. The Th epitopes may be intrinsic to the peptide or added thereto as described in the prior art. Suitable peptide immunogens are described hereinbelow.

An "anionic molecules" as described herein refers to molecules, which are negatively charged at a pH in the range of 5.0-8.0. The net negative charge on the oligomer or polymer is calculated by assigning a −1 charge for each phosphodiester or phosphorothioate group in the oligomer. A suitable anionic oligonucleotide is a single-stranded DNA molecule with 8 to 64 nucleotide bases, with the number of repeats of the CpG motif in the range of 1 to 10. Preferably, the CpG immunostimulatory single-stranded DNA molecules contain 18-48 nucleotide bases, with the number of repeats of CpG motif in the range of 3 to 8.

More preferable the anionic oligonucleotide is represented by the formula: 5' $X^1CGX^2$ 3' wherein C and G are unmethylated; and $X^1$ is selected from the group consisting of A (adenine), G (guanine) and T (thymine); and $X^2$ is C (cytosine) or T (thymine). Or, the anionic oligonucleotide is represented by the formula: 5' $(X^3)_2CG(X^4)_2$ 3' wherein C and G are unmethylated; and $X^3$ is selected from the group consisting of A or G; and $X^4$ is C or T.

Most preferably, the CpG oligonucleotide is selected from a group consisting of 5' TCG TCG TTT TGT CGT TTT GTC GTT TTG TCG TT 3' (CpG1) SEQ ID NO: 1, a 32 base length oligomer, and 5'nTC GTC GTT TTG TCG TTT TGT CGT T 3' (CpG2) SEQ ID NO: 2, a 24 base length oligomer plus an phosphorothioate group (designated as n at the 5' end).

The resulting immunostimulatory complex is in the form of particles with a size typically in the range from 1-50 microns and is a function of many factors including the relative charge stoichiometry and molecular weight of the interacting species.[32] The particles of immunostimulatory complex has the added advantage of providing adjuvantation and upregulation of specific immune responses in vivo. Additionally, the stabilized immunostimulatory complex is suitable for preparing vaccine formulations by various processes including water-in-oil emulsions and polymeric gels.

The term "stabilize" as used herein may be accomplished by the use of any material, which protect the synthetic peptide immunogen against degradation in vitro or in vivo. The term "stabilize" as used herein may be accomplished by the use of any material, which protect the synthetic peptide immunogen against degradation in vitro or in vivo. This may be accomplished by virtue of chemical modification and/or physical association. A stabilizer may augment the physiological properties of a synthetic peptide immunogen, a oligosaccharide-modified glycopeptide or a lipidated peptide to provide a more efficacious formulation.

The term "adjuvant" as described herein refers to any material, which can enhance or upregulate the immune responses elicited by an immunogen in humans or animals. The adjuvant itself may or may not induce an immunogenic response.

The stabilizer may also preferably function in a vaccine as an adjuvant, effectively upregulating the immune responses. The stabilizer may act as an adjuvant by actively facilitating the presentation of the immunogen to professional processing cells of the immune system, such as macrophages and dendritic cells. In the present invention, the stabilized immunostimulatory complex ideally remains as an integral unit in solution when administered.

The stabilized immunostimulatory complex may also be formulated for controlled release and remains as a complex in a concentrated form in a "depot" near the site of administration. These formulations synergistically combine the benefits of a stabilized adjuvanted immunogen coupled with a sustained local release of immunogen to immune effector cells. In some compositions the role of the adjuvant itself may also involve attracting cells of the immune system to the vicinity of the immunogen depot and stimulate such cells to elicit an immune response.

In a second aspect of this invention, there is provided a method for preparing a vaccine composition containing an immunostimulatory complex. In a preferred embodiment the immunostimulatory complex has the added advantage of being a stabilized synthetic peptide-based immunogen in vitro and at the same time is self adjuvanting with upregulation of specific immune responses in vivo.

In a third aspect of this invention, there is provided a method for preparing a vaccine composition from the immunostimulatory complex. The immunostimulatory complex or a mixture of the immunostimulatory complex with the uncomplexed immunogen may be formulated as a suspension in solution, a water-in-oil emulsion, or a reconstituted suspension in a biocompatible solution. The immunostimulatory complex alone or in a mixture with uncomplexed immunogens may also be co-formulated in a biocompatible solvent in a polymeric gel.

This invention is further directed to the production of useful immunogen delivery systems for administration by various routes, including parenteral, oral, intranasal, rectal, buccal, vaginal and transdermal routes.

BRIEF DESCRIPTION OF THE DRAWINGS

The present invention is further understood with reference to the drawings.

DETAILED DESCRIPTION OF THE INVENTION

Figure 1:
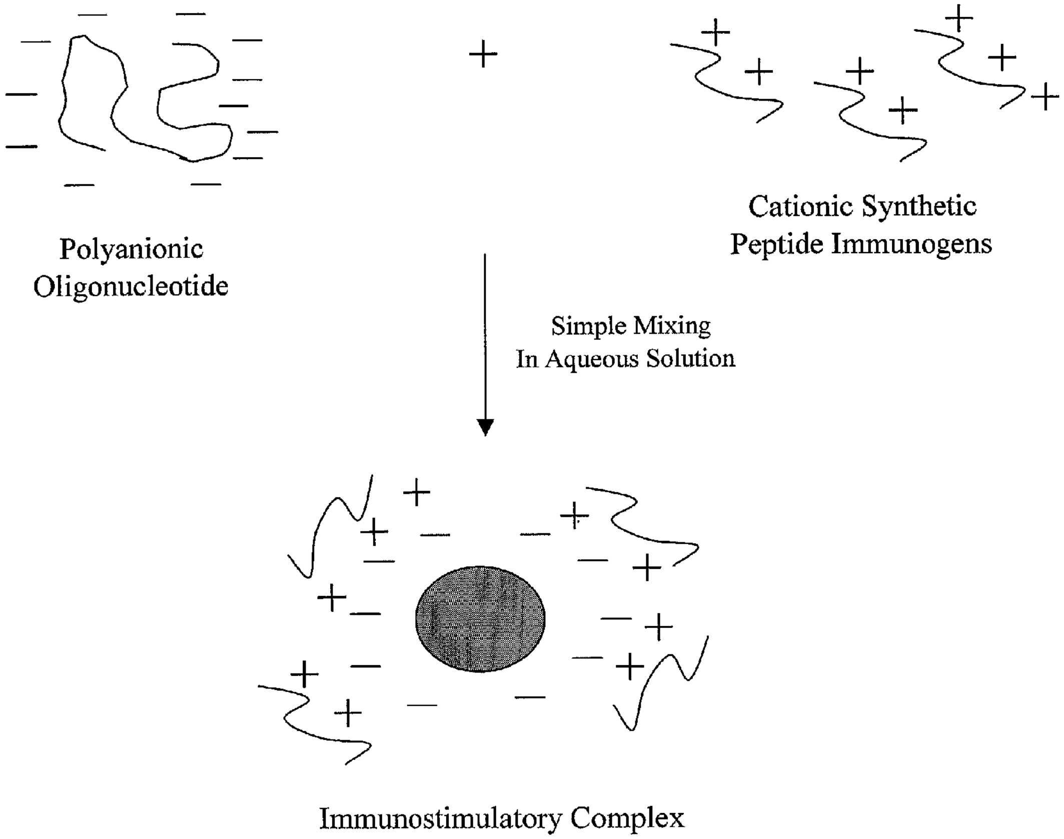
FIG. 1 is a schematic showing the complexation process of cationic peptide immunogens and CpG oligonucleotides.

In accordance with a first aspect of the invention, a cationic peptide immunogen is complexed with an anionic single-stranded DNA to form a stable immunostimulatory complex.

The cationic peptide immunogen is a peptide with a net positive charge at a pH in a range of 5.0 to 8.0. The net charge on the peptide or peptide cocktails is calculated by assigning a +1 charge for each lysine (K), arginine (R) or histidine (H), a −1 charge for each aspartic acid (D) or glutamic acid (E) and a charge of 0 for the other amino acids in the sequence. The charge contributions from the N-terminal amine (+1) and C-terminal carboxylate (−1) end groups of each peptide effectively cancel each other when unsubstituted. The charges are summed for each peptide and expressed as the net average charge. Preferably, the net average charge of the peptide immunogen is at least +2.

The cationic peptide immunogen may have a net positive charge intrinsically as calculated above based on its amino acid sequence. It may be made to have a positive charge by the addition of a lysine, an arginine or a histidine or a mixture of these amino acids to the N-terminal or C-terminal of the peptide immunogen. Other synthetic moieties, such as polyethyleneimine or polyamines, which provide a positive charge to the peptide immunogen in aqueous solution, may also be added.

The cationic peptide immunogen comprises a Th epitope and a target B-cell epitope. The Th epitope may be intrinsic to the peptide or may be synthetically added to a peptide, which functions as a target B-cell epitope. Suitable peptide immunogens include peptides that elicit protective or therapeutic immune responses and are derived from pathogens or proteins known to cause diseases. These include: human or animal IgE peptides for the immunotherapy of allergies, e.g., the IgE peptide immunogens described in WO 99/67293[51]; HIV peptides for protective immunity and immunotherapy for HIV infection described in U.S. Pat. No. 5,763,160[52]; CD4 peptides for protective immunity from HIV and immunotherapy of HIV infection and immune disorders described in U.S. Pat. No. 6,090,388[53]; Luteinizing Hormone Releasing Hormone (LHRH) peptides for immunotherapy of androgen and estrogen-dependent tumors, contraception and immunocastration, and removal of boar taint described in U.S. Pat. No. 5,759,551[54] and U.S. Pat. No. 6,025,468[55]; β-amyloid peptides for prevention and immunotherapy of Alzheimer's Disease described in U.S. Ser. No. 09/865,294[56]; foot-and-mouth disease virus peptides for protective immunity against foot-and-mouth disease described in U.S. Pat. No. 6,107,021[57]; peptides from bacterial pili for protective immunity from urinary tract infection described in U.S. application Ser. No. 09/747,802[58]; Plasmodium peptides for protective immunity from malaria described in WO 99/66957[59]; and somatostatin peptides for growth promotion in livestock described in WO 99/66950.[60] The specific peptide immunogens named herein are examples for purposes of illustration only and are not to be construed as limiting the scope of the invention in any manner.

The "anionic single stranded DNA" is a polynucleotide or oligonucleotide that is negatively charged at a pH in the range of 5.0-8.0. The net negative charge on the polynucleotide or oligonucleotide is calculated by assigning a −1 charge for each phosphodiester or phosphorothioate group in the oligomer. A suitable anionic oligonucleotide is a single-stranded DNA molecule with 8 to 64 nucleotide bases, with a repeated CpG motif and the number of repeats of the CpG motif is in the range of 1 to 10. Preferably, the CpG immunostimulatory single-stranded DNA molecules contain 18-48 nucleotide bases, with the number of repeats of CpG motif in the range of 3 to 8.

Preferably, the anionic oligonucleotide is represented by the formula: 5' $X^1CGX^2$ 3' wherein C and G are unmethylated; and $X^1$ is selected from the group consisting of A (adenine), G (guanine) and T (thymine); and $X^2$ is C (cytosine) or T (thymine). Or, the anionic oligonucleotide is represented by the formula: 5' $(X^3)_2CG(X^4)_2$ 3' wherein C and G are unmethylated; and $X^3$ is selected from the group consisting of A or G; and $X^4$ is C or T. The CpG oligonucleotide may be modified at the 5' end with a phosphorothiorate or a thiol-acetamido glycopolymer.[34]

Most preferably, the CpG oligonucleotide is selected from a group consisting of 5' TCG TCG TTT TGT CGT TTT GTC GTT TTG TCG TT 3' (CpG1) SEQ ID NO: 1, a 32 base length oligomer, and 5'nTC GTC GTT TTG TCG TTT TGT CGT T 3' (CpG2) SEQ ID NO: 2, a 24 base length oligomer plus an phosphorothioate bridging group (designated as n at the 5' end).

It is known that the DNA sequences derived from unmethylated cytosine-guanine (CpG) dinucleotides activate lymphocytes and can enhance a subject's immune responses, including IL-6, TNF-α, IL-12, IFN-γ responses[33]. Based on this finding, these molecules represent preferred complementary substrates that can both stabilize the synthetic cationic peptide immunogens and provide a novel immunogen delivery system. Moreover, the immunostimulatory complexes of the present invention provide self-adjuvantation of the immune responses in vivo without significant dilution at the site of injection.

The formation of discrete immunostimulatory complexes derived from cationic peptide immunogens is principally a function of charge neutralization. It is expected that stable complexes may be formed from CpG-containing immunostimulatory DNA molecules derived from both natural or synthetically modified nucleotide sequences. Furthermore, improvements in the stability of an immunostimulatory complex may be realized by increasing the cationic charge residing on the peptide immunogen. These include extending the peptides with additional lysine, arginine or histidine or other synthetic moieties, which provides a positive charge to the modified peptide in an aqueous solution as described above.

Modified CpG motifs are also envisioned, wherein a defined anionic single-stranded DNA has been chemically conjugated to another biologically functional molecule, such as lectins, sugars or lipids for enhancing cell specific uptake and targeting or polymers, copolymers and graft copolymers such as PEG for improved circulation in vivo. The chemically conjugated DNA may be polyanionic and may subsequently be complexed with a cationic peptide immunogen to provide a modified immunostimulatory complex with potentially novel physical or biological properties.[34, 35]

It is contemplated that block and graft co-polymers derived from polyanionic oligomers and polyethylene glycol represent another class of anionic molecules, which may also provide improved stability and improved adjuvanticity.

In another aspect of this invention an immunostimulatory complex may be prepared from a modified CpG oligonucleotide, wherein an additional phosphorothioate or another bridging group has been added at the 5' end of the oligomer for improved complexation.

Preferably, the immunostimulatory complex have an average aggregate particle size distribution in the range of about 1 to 50 μM. More preferably, the immunostimulatory complex have an average aggregate particle size distribution in the range of about 1 to 30 μM. Most preferably, the immunostimulatory complex have an average aggregate particle size distribution in the range of about 1 to 15 μM.

There is evidence that the number of CpG motif repeats influences the degree of intrinsic adjuvanticity and immune stimulation, with a minimum number of CpG repeats being required. Moreover, there is strong evidence that the selection of flanking nucleotide bases adjacent to the CpG is very important, as this appears to directly impact the adjuvanticity in a species-specific manner.[10, 36] For example, it was demonstrated by Kreig et al.[13] that enhanced immunostimulatory activity of human cells occurred when oligonucleotides containing CpG motifs are represented by the formula $X^1X^2CGX^3X^4$ where C and G were unmethylated, and $X^1X^2$ were selected from the groups GpT, GpG, GpA and ApA and/or $X^3X^4$ were selected from the groups TpT, CpT and GpT.

Although CpG oligonucleotides can function as B-cell mitogens[37] and are useful adjuvants, it has been shown that the immune responses generally peak 2 weeks after administration for an antigen mixed with CpG oligonucleotides in a soluble form. This necessitates multiple repeat injections to maintain high antibody titers to ensure protection.[38] Thus, a method for effectively delivering constructs with these oligonucleotides in a controlled release formulation is strongly desired.

With respect to stability, the phosphodiester bond in the CpG backbones are sensitive to degradation by nucleases in vivo[39]. Thus to improve the duration of the immune response, the phosphate groups may be modified to phosphorothioate groups.

The immunostimulatory complex of the present invention may be formulated for delivery by numerous pathways including parenteral, mucosal and transdermal. The immunostimulatory complex of the present invention is particularly desirable for vaccine formulations in that the CpG oligonucleotides in the complex are useful adjuvants for upregulating both parenteral and mucosal responses in vivo.[40, 41]

The results of our experiments show that the particle size of the immunostimulatory complex varies based on the ratio of the peptide immunogen to the CpG oligonucleotide. The intrinsic stability of the immunostimulatory complex and the ability to control the size of the composition increases the potential for phagocytosis by a parenteral route.[19] Mucosal immunization by targeting specific cells, such as M-cells located on Peyer's Patches via oral route[21] or the nasal-associated lymphoid tissue (NALT) via intranasal route[23] is similarly facilitated by the use of the stabilized immunogen of the present invention.

The immunostimulatory complex of the present invention is prepared by a controlled self-assembling process wherein the anionic CpG oligonucleotide in aqueous solution is added to an aqueous solution of the cationic peptide immunogen. Suitable aqueous solutions for the preparation of an immunostimulatory complex is selected from the group consisting of distilled deionized water (DDW), normal saline (NS) or phosphate buffered saline (PBS). Distilled deionized water and normal saline typically exhibits a pH of about 5.5, whereas in PBS, the pH is controlled in a range of 7.2-7.4. The complexation process is a function of the charge ratios, the molecular weight of the interacting electrolytes, pH and ionic strength of the medium.[32]

Multiply charged anionic molecules, such as the short CpG oligomers possess a net negative charge when the pH is in the range 5.5-7.4 in aqueous solutions. The net charge on the peptide immunogen is dependent on the amino acid composition of the peptide and may be affected by the pH of the aqueous solution. Thus, the aqueous medium is selected to ensure a net positive charge for efficient complexation. An examination of the ionization point (IP) or point of zero charge for the individual peptides can guide the selection process. The IP is determined by the motion of the molecule through a pH-gradient in an isoelectric focusing experiment.[11] To ensure a peptide is positively charged, the pH of the selected aqueous medium should be less than the isoelectric point for the peptide in question.

To prepare an immunostimulatory complex the following steps are followed. Firstly, the average molar positive charge contribution is determined for a desired peptide immunogen or for a cocktail of peptide immunogens based on the molar ratios of peptides mixed together and the charge contribution from each peptide component in the final vaccine composition. Secondly, the molar negative charge contribution is determined for the complexing oligonucleotide based on the molar ratio of oligomer and the charge contribution from this component in the final vaccine composition. Thirdly, the amount of peptide immunogen, based on total average molar positive charge, is dependent on the amount of oligonucleotide employed for complexation and the total molar negative charge thereof. This relationship is used to define the relative amounts of peptide immunogens and oligonucleotides to be combined in an aqueous solvent to form an immunostimulatory complex. An excess of the cationic immunogen peptide may be employed to provide a mixture of the immunostimulatory complex and an excess of the uncomplexed peptide. Or, an excess of the oligonucleotide may also be employed to provide an excess of the oligonucleotide. The relative amounts of the peptide immunogen and the oligonucleotide is selected based on the vaccine formulation desired.

Finally, the calculated amount of anionic oligonucleotide in a compatible aqueous solvent is added with mixing to the calculated amounts of cationic peptide immunogens similarly dissolved in a compatible aqueous solvent. The amount in nmol of the cationic peptide immunogen used is generally in a range to provide 8 positive charges to 0.5 positive charge to the amount in nmol of the anionic oligonucleotide to provide one negative charge. This is referred to as the charge ratio. Where the charge ratio is 8:1, there is a large excess of the peptide immunogen. Where the charge ratio is 1:2, there is a moderate excess of the anionic oligonucleotide. The complex forms spontaneously in the form of a suspension in solution. Estimation of the residual amounts of peptide immunogens or oligonucleotides can be made by separating the complex from the solution and assaying the supernatant solutions by ultraviolet spectrophotometry.

The immunostimulatory complex as prepared as a suspension may be used as a vaccine composition. If the immunostimulatory complex is to be injected parenterally, the aqueous solvents are selected such that the final vaccine composition is isotonic and suitable for such a purpose, In cases where the complex is first formed in distilled deionized water, aqueous buffers of suitable salt concentration are added to ensure the final vaccine composition is isotonic.

The immunostimulatory complex prepared as a suspension or solution may be lyophilized. The lyophilized composition may then be reconstituted and incorporated into different vaccine formulations in accordance with the desired mode of delivery. The immunostimulatory complex of the present invention may also be formulated as a water-in-oil emulsion or a biocompatible polymeric gel.

In accordance with a further aspect of the invention, the invention describes a process for isolating the stabilized immunostimulatory complexes as stable particles via lyophilization. Reconstitution of the stabilized immunostimulatory complex as a suspension in aqueous solvents or biocompatible solvents shows essentially no changes in the particle size distribution or in vivo potency. This represents an important advantage over formulations requiring refrigeration to maintain efficacy, such as Alum-based vaccine compositions. This feature extends the potential utility of these systems to include direct reconstitution prior to immunization and alternative modes of delivery which require stable solid state dosage forms, such as a dry powder aerosol or nebulization for pulmonary or intranasal delivery.[42]

In accordance with a further aspect of the present invention, the invention provides various processes for preparing stable water-in-oil emulsions[43] comprising the stabilized immunostimulatory complex of the present invention. In such an emulsion, preferably the aqueous phase comprises the immunostimulatory complex or a mixture of the immunostimulatory complex with the uncomplexed peptide immunogen; and the continuous oil phase comprises a synthetic, mineral, animal or vegetable oil. Additionally, the oil phase may also comprise an immunostimulatory emulsifier, a biocompatible or a metabolizable component.

In particular, the oils useful for preparing the water-in-oil emulsions of the present invention include, but are not limited to, synthetic oils (e.g. isopropyl myristate), vegetable oils (e.g. peanut oil), mineral oils (e.g. Drakeol™ or Marcol™), metabolizable animal oils (e.g. squalene or squalane), and a mixture thereof. The mineral oils are preferred. The oil-based emulsifiers useful for stabilizing the emulsions include, but are not limited to, the family of mannide oleates and derivatives thereof.

The relative amount of emulsifier required is a function of the hydrophile-lipophile balance (HLB) and the intrinsic stability of the water-in-oil emulsion produced under specified conditions. Methods for selecting oils and combinations of emulsifiers are well known to those skilled in the art.

The w/o-emulsion may comprise between 10 v/v % and 80 v/v % water in the internal aqueous phase. For most purposes, the optimal water concentration is in the range of 30 v/v % and 50 v/v %. The internal aqueous phase is characteristically comprised of very fine droplets with sizes typically in the range of 1-10 μM, preferably 1-5 μM. The preparations are stable when maintained at room temperature or refrigerated.

Other stabilizing agents may also be used to prepare the emulsion. These include surfactants, colloidal particles, proteins, and other polymerizing and stabilizing agents known to those skilled in the art.

The w/o-emulsion may further comprise at least one oil-soluble lipophilic adjuvant. The w/o-emulsion may also comprise at least one water-soluble adjuvant, which may be synthetic or natural, in the dispersed phase. The presence of a water-soluble adjuvant with film forming properties, such as an oligomer or polymer, can additionally serve to stabilize the emulsion. The w/o-emulsion can facilitate presentation of the immunogens to the immune system to provide a more efficacious vaccine.

A water-in-oil emulsion comprising an immunostimulatory complex, or a mixture thereof with uncomplexed immunogen may be prepared as follows. Firstly, an immunostimulatory complex is prepared from a peptide immunogen and an oligonucleotide in a ratio to ensure the formation of the immunostimulatory complex alone or in a mixture with excess residual peptide immunogen in an aqueous solution. Secondly, the aqueous solution is mixed with an oil containing emulsifiers and homogenized to provide a water-in-oil emulsion wherein the aqueous phase is dispersed in a continuous oil phase. The water-in-oil emulsion as such is suitable for parenteral injection.

Emulsification of the aqueous and oil phases can be accomplished by homogenization or by transfer between two syringes or by extruding the components through a membrane filter of a controlled pore size. The low-energy semi-manual methods are rapid. However, because there is considerably less shear than other processes, the emulsion produced is not as fine as that produced using high shear mechanical systems. Examples of high-shear systems include rotostators, microfluidizers, and sonifiers. Other devices similar to these high-shear systems that are well known for emulsification may also be employed.

In accordance with another aspect of this invention, there is provided a process for preparing an in-situ gelling biodegradable polymer in which a stabilized immunostimulatory complex or a mixture of a stabilized immunostimulatory complex and uncomplexed immunogen is dispersed. The immunostimulatory complex may be dispersed either in solution or as a suspension within a biocompatible solvent. The biocompatible solvent may further comprise a soluble adjuvant that is synthetic or natural. The solution or suspension in the biodegradable gelling polymer is designed for the delivery of the immunogen to a host. The in-situ gelling polymer is biodegradable and is a copolymer of poly-D,L-lactide-co-glycolide (PLG) and poly-D,L-lactic acid-co-glycolic acid (PLGA) with a molecular weight in the range of about 2,000 to about 100,000 daltons and an inherent viscosity of about 0.2 to 1.0 dl/g. The formula of the in-site gelling polymer is:

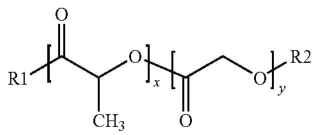

R1 = OAlkyl (PLG) or OH(PLGA)
R2 = H wherein R1 is OH or alkoxy having 1 to 5 carbons and R2 is H; x:y is the ratio of each monomer unit of the copolymer with x+y=1.

In the case of PLG, R1 is alkoxy and the monomer units are lactide and glycolide and in the case of PLGA, R1 is OH and the monomer units are lactic acid and glycolic acid.

The stabilized immunostimulatory complex or a mixture thereof with the uncomplexed immunogen with the in-situ gelling polymer may be prepared as a single phase or as a suspension in a biocompatible solvent.

The biocompatible solvent useful in the present invention is selected from the group consisting of dimethyl sulfoxide (DMSO), N-methyl pyrrolidine (NMP), triacetin and glycerin. DMSO is preferred. DMSO has a high capacity for solubilizing a large quantity in weight percent of the polymer. It has been widely used as a solvent for in-situ gelling of polymers. DMSO may be also be used to prepare a suspension of the stabilized immunostimulatory complex of the present invention.

Importantly, it has been demonstrated in animal models that there is a high tolerance for DMSO when used in small amounts.[44] Thus, toxicity concerns are minimal when compositions comprising DMSO are administered via a parenteral route.

The biodegradable polymers suitable for the present invention include, but not limited to, the PLA or PLGA family of polyesters. These materials can be dissolved in various biocompatible solvents at a concentration in a range of 5 w/w %-50 w/w %. Several physical factors can influence the practical amount of polymer, which may be dissolved in the biocompatible solvent. These include the constitution, molecular weight, intrinsic viscosity and crystallinity of the polymer. For the PLG/PLGA series of copolymers, these factors are highly variable. For example, homopolymers of either poly D,L-lactic acid (PLA) or poly D,L-lactide (PL) and copolymers of PLG or PLGA with long blocks of the lactic acid monomer component are highly crystalline materials with relatively high intrinsic viscosities.

The relative weight percentage of these crystalline materials which can be solubilized is distinctly lower than the amorphous PLG or PLGA analogs, wherein the ratio of the lactic acid to glycolic acid components are approximately equal, 1:1. It is contemplated that the difference in the total amount of polymer, which may be administered by injection, will have a dramatic impact on the matrix degradation rate and affect the release kinetics for encapsulated immunogens. It is envisioned that it is possible to vary the blends of physically compatible polymers and copolymers with varying physical properties in biocompatible solvents to achieve novel biological effects.

Other biodegradable polymers suitable for the present invention are contemplated and include, but are not limited to, polycaprolactones, polyanhydrides, polyorthoesters and poly (α-hydroxybutyric acid). These polymers can be solubilized in biocompatible solvents at useful weight percentages and provide useful matrix-forming substrates.

In accordance with the present invention, a controlled or delayed release vaccine preparation in stable form is provided together with a method of making such a vaccine preparation. The gel matrix of the controlled or delayed release vaccine composition comprise a biodegradable polymer selected from the group consisting of poly-D,L-lactide-co-glycolide (PLG) and poly-D,L-lactic acid-co-glycolic acid (PLGA), polycaprolactones, polyanhydrides, polyorthoesters and poly (α-hydroxybutyric acid), a biocompatible solvent and a stabilized immunostimulatory complex.

Advantages of the controlled released composition of the present invention include:

(a) a fully biodegradable and biocompatible gel formulation;

(b) a sustained release of the immunogen for presentation to the immune effector cells resulting in improved immunogenicity;

(c) a high loading of the gel with a desired immunogen in a stable composition; and (d) a flexible modes of delivery including a suspension of a stabilized immunostimulatory complex that is self-adjuvantated.

The molecular weight and crystallinity of the polymer directly impacts the entrapment efficiency in vivo. The polymeric gelling material is miscible in polar aprotic solvents such as DMSO. However, upon intramuscular or subcutaneous injection, DMSO is extracted into the surrounding body tissues with water reversibly penetrating the polymer rich solution. This process serves as the primary mechanism controlling in-situ gel formation. The rate at which this process proceeds directly affects the initial burst of release of the immunogen during the time interval when the biocompatible solvent is actively extracted into body tissue and exchanged with physiological solutions and before the entrapment of the immunogen by the formation of the gel.[45] It is known that controlling the crystallization process is an important key mechanism by which the retention of immunogens within the gel can be improved.[46] This is intimately connected to the internal morphology of the gel formed, which limits the diffusional pathways by which immunogens may be released.

The entrapped or retained immunostimulatory complexes are subsequently released from the gel in limiting amounts in a sustained fashion with a larger boost released when the bulk of the matrix forming polymer is eroded. This varies depending on many of the same conditions that influence gellation, such as molecular weight, degree of crystallinity, constitution, hydrophobicity, and the presence of additives.

The potential for an adverse toxicological response to the solvent DMSO has been addressed in a recent study[44] wherein a device containing a peptide hormone suspended in DMSO was surgically implanted subcutaneously in a dog and in a human. The volume of DMSO employed in the study was 150 μL. The implant was designed to release the peptide over the course of 1 year and surgically removed at the end of the study. In neither the dog or the human were any adverse tissue reactions observed. The controlled release of the peptide/DMSO mixture from the implant into physiological tissues is useful as a model for evaluating potential toxicity concerns for a fully biodegradable in-situ gelling polymeric composition. It is contemplated that the amount of DMSO useful in the present invention is essentially the same as that used in the study.

It is expected that there is an initial extraction of the immunostimulatory complex in DMSO into body tissue before the solubility limit of the polymer is exceeded. Solidification takes place, retarding the release of the stabilized immunostimulatory complex. Subsequently, the stabilized immunostimulatory complex is released along with DMSO by diffusion-controlled pathways or retained in the gel with a release rate that is a function of the polymer properties. It is apparent that the diffusivity of these molecules within the gel is governed by several factors, such as the internal gel morphology and porosity, the degree of penetration by water into the gel and the hydrolysis of the bulk of the polymer.[45]

In the case of the stabilized immunostimulatory complex of the present invention, which is dispersed as a suspension throughout the gel, the initial extraction is largely that of DMSO with a small quantity of the immunostimulatory complex located near the gelling front. Thus, the small amount of the immunostimulatory complex, not effectively entrapped during the initial gelling phase, would be responsible for the initial priming of the immune response in vivo. Thereafter, it is expected that DMSO would continue to be released by diffusion, with the bulk of the immunostimulatory complex remaining entrapped in the gel matrix until the bulk of the polymer has sufficiently been hydrolyzed to result in a full release of the encapsulated immunostimulatory complex.

Specifically, polymeric gels formulated from higher molecular weight and more crystalline polymers derived from (α-hydroxy acids degrade over a longer period of time than lower molecular weight amorphous analogs. This phenomena, is known to be related to the accessibility of water to the hydrolytically unstable ester bonds.[46]

It has been established that random amorphous copolymers composed of 50% D,L-lactide and 50% glycolide with a molecular weight in the range of from 8,000-50,000 daltons exhibit the highest degradation rates. 50% by weight or less of the polymer remains after approximately 6-8 weeks, when immersed in a PBS buffer.[47]

It is desirable to modify the parameters controlling the rate of gellation, the kinetics of immunogen release and the internal gel morphology. Specifically, use of various pore forming agents, plasticisers, and stabilizers such as surfactants, sugars, proteins, polymers and other excipients known to those skilled in the art are useful for this purpose.

The preparations are stable when refrigerated or at room temperature. The vaccine composition of the present invention employing DMSO will freeze when refrigerated since the freezing point of DMSO is about 18° C. It has been found that thawing does not cause a change in the efficacy of the vaccine in vivo.

In accordance with the present invention, the in-situ gelling biodegradable polymer and the stabilized immunostimulatory complex may be formulated separately. The in-situ gelling polymer may be solubilized in a biocompatible solvent in one vial, and the stabilized immunostimulatory complex in dry form in a separate vial. The immunostimulatory complex in dry form may be prepared by spray-drying, or preferably, lyophilization.[48, 49] The dried immunostimulatory complexes can then be reconstituted in a biocompatible solvent, and dispensed by syringe either as a solution or as a suspension into the biodegradable polymer solution. The mixture is then used immediately, or soon thereafter for immunization.

Employing separate vials has an added advantage of minimizing any potential stability problems. These include polymer degradation in the presence of the peptide immunogen, which may have reactive functional side chains, such as, free amine groups or carboxylate groups,[50] or the oxidation of selective amino acids, such as cysteine and tryptophan in the peptide immunogen in the presence of DMSO.[1]

To prepare a reconstitutable in-situ gelling polymer composition containing an immunostimulatory complex, an immunostimulatory complex is prepared as described above. Then, this aqueous solution is lyophilized to form a dried composition. The dried composition is then reconstituted as a suspension in a biocompatible solvent containing a calculated weight percentage of a biodegradable gelling polymer. The final vaccine composition represents an in-situ gelling polymer and is suitable for parenteral injection.

The compositions of the present invention are contemplated to be useful as vaccines or for therapeutic purposes. Other biological materials which may be modified to possess cationic charge at pH's generally ranging from 4.0-8.0 for efficient complexation with CpG oligonucleotides, may include proteins, protein mimetics, bacteria, bacterial lysates, viruses, virus-infected cell lysates, antigens, antibodies, pharmacological agents, antibiotics, carbohydrates, lipids, cytokines, chemokines, lipidated amino acids, glycolipids, haptens and combinations and mixtures thereof.

These compositions can be administered parenterally via subcutaneous or intramuscular injection. When administered, parenterally, the immune response may be a cell mediated response or a local or serum antibody response to provide neutralizing antibodies. For compositions administered mucosally the immune responses would additionally include a local secretory antibody response.

It will be readily apparent to those skilled in the art that further the immunostimulatory complexes may also be formulated to be sequentially admixed or adsorbed to mineral salts such as Aluminum hydroxide or Aluminum phosphate or admixed in oil-in-water (o/w)-based emulsions. Encapsulation of stabilized immunostimulatory complexes within water-in-oil-in-water (w/o/w) double emulsions, biodegradable polymeric microparticles, lipid vesicles or liposome structures are particularly attractive for sustained release formulations.

Preferably, the peptide immunostimulatory complex of the present invention may be employed in w/o-based emulsions or in a single-dose controlled release in-situ gelling formulation based on biodegradable poly-D,L-lactide-co-glycolide (PLG) or poly-D,L-lactic acid-co-glycolic acid (PLGA) copolymers.

Most preferably, the vaccine compositions of the present invention comprise a stabilized immunostimulatory complex of the peptide immunogen with a CpG olionucleotide admixed with the uncomplexed peptide immunogen.

It is clearly apparent to one skilled in the art, that the various embodiments of the present invention have many applications in the fields of medicine and in particular vaccination, diagnosis and treatment of infections with pathogens including bacteria and viruses. Further uses of the present invention are described below.

Vaccine Preparation

Immunogenic compositions, suitable to be used as vaccines, may be prepared from an immunostimulatory complex of the present invention, as a w/o emulsion, as an in-situ gelling polymer or a combination of these systems as disclosed herein. The immunogenic composition containing the immunostimulatory complex is useful for eliciting an immune response by the host to which it has been administered. The immune response includes the production of antibodies by the host.

The immunogenic composition may be prepared as injectables, as liquid solutions or suspensions, as lyophilized or spray-dried powders or emulsions. The composition comprising the immunostimulatory complex may be mixed with physiologically acceptable buffers or excipients, such as, water, saline, dextrose, glycerol, ethanol and combinations thereof. The vaccine may further contain additional substances such as wetting or emulsifying agents, pH buffering agents, or adjuvants to further enhance the effectiveness thereof. The vaccine may further contain additional biocompatible substances, specifically in conjunction with the in-situ gelling polymers such as dimethyl sulfoxide (DMSO), N-methyl pyrrolidine (NMP), triacetin, glycerin, and poly vinyl pyrrolidone (PVP).

The vaccine of the present invention may be administered parenterally, or by injection subcutaneously or intramuscularly. The vaccines of the present invention may be administered mucosally via oral, intranasal, rectal, vaginal or ocular routes.

The vaccines are administered in a manner compatible with the formulation, and in such amount as to be therapeutically effective, protective and immunogenic. The quantity to be administered depends on the subject or species to be treated, including, for example, the capacity of the subject's or species' immune system to synthesize antibodies, and if needed, to produce cell-mediated immune responses.

Precise amounts of emulsifying oils or gelling polymers and material having biological activity required to be administered for effect depend on the judgement of the practitioner or veterinarian. However, suitable dosage ranges are readily determinable by one skilled in the art and may be of the order of micrograms to milligrams. Suitable regimes for initial administration and booster doses are also variable, but may include an initial administration followed by subsequent administrations. The dosage of the vaccine may also depend on the route of administration and thus vary from one host or species to another.

EXAMPLES

The above disclosure generally describes the present invention. A more complete understanding can be obtained by reference to the following specific Examples. These Examples are described solely for purposes of illustration and are not intended to limit the scope of the invention. Changes in the form and substitution of equivalents are contemplated as circumstances may suggest it as necessary to achieve a particular goal. Although specific terms have been employed herein, such terms are intended in a descriptive sense and not for purposes of limitations.

Methods of chemistry, organic chemistry, polymer chemistry, protein biochemistry and immunology used but not explicitly described in this disclosure and these Examples are amply reported in the scientific literature and are well within the ability of those skilled in the art.

Preparation of Immunostimulatory Complex

In general, an immunostimulatory complex of a synthetic peptide immunogen and a CpG oligonucleotide in aqueous solutions is prepared by the dropwise addition of a stock peptide solution in an appropriate aqueous solvent into a vial containing a gently stirred stock solution of CpG oligonucleotide dissolved in an appropriate aqueous solvent. The reverse mode of addition is equally effective. Compatible aqueous solvents include, but are not limited to, distilled deionized water, normal saline (NS=0.9% NaCl) or phosphate buffered saline (PBS=10 mM Phosphate buffer, 0.9% NaCl) or mixtures thereof. The complexation process is largely unaffected by physiologic buffers, providing flexibility when selecting a compatible solvent system for both the synthetic peptide immunogen and the CpG oligonucleotide.

The complex forms immediately and can be identified visually by the observation of a fine precipitate suspended in solution. The quantity of suspension so formed is a function of the relative amounts of the CpG oligonucleotide to the cationic peptide in solution. The precipitation process is controlled by the electrostatic neutralization of oppositely charged molecules. In a thermodynamically favourable process, the highly charged polyanionic single-stranded DNAs bind with the positively charged cationic peptide immunogen.[61]

The CpG oligonucleotide is selected from a group consisting of 5' TCG TCG TTT TGT CGT TTT GTC GTT TTG TCG TT 3' (CpG1) SEQ ID NO: 1, a 32 base length oligomer, and 5'PhTC GTC GTT TTG TCG TTT TGT CGT T 3' (CpG2) SEQ ID NO: 2, a 24 base length oligomer plus an phosphorothioate group (designated as Ph at the 5' end). The CpG oligonucleotides were synthesized by Oligo's Etc. (Wilsonville, Oreg.), and are obtained in a lyophilized dry state. These materials were reconstituted in the appropriate aqueous solvent prior to use. CpG1 possesses a CpG motif sequestered within a sequence of 8 nucleotide bases and may provide stronger adjuvantation in vivo and improved stability by binding cationic peptides with higher affinities, than shorter oligonucleotides. A phosphorothioate or a thiol modified group at the 5' end of CpG2 increase the molar charge density and thereby potentially promote improved binding.

The peptide immunogens were synthesized and the appropriate aqueous buffer used to ensure that the peptide is cationic in solution. This is an important consideration in vaccines where complexation of the peptide immunogen to the CpG oligonucleotide is desired. The ionization point or IP for each peptide immunogen and the pH of the medium is used to guide the selection of the appropriate buffer. The pH for an aqueous mixture of a stock peptide solution dissolved in distilled deionized water or normal saline (NS) was approximately 5.5, whereas in phosphate buffered saline (PBS) the pH of the stock peptide solutions was significantly higher at approximately 7.2. Careful selection of aqueous solvent systems is made to ensure full protonation for peptides derived from amino acids with weakly basic side chains, notably Histidine.

Table 1 list the physical properties of the synthetic peptide immunogens and CpG oligonucleotides, used to form immunostimulatory complexes. Three exemplary peptide immunogen targets are depicted in Table 1. A cocktail of two or three peptide immunogens have been employed to prepare each vaccine. Each peptide immunogen comprises two segments, a B-cell target epitope and a T-helper epitope. The Th epitope is included to improve the immunogenicity of the peptide immunogen.

The B-cell and T-help epitopes were selected after screening libraries of peptides in the appropriate animal models. Detailed information regarding the identification and composition of these constructs can be found by referring to U.S. Pat. No. 6,090,388[53], U.S. Pat. No. 5,759,551[54] and WO99/67293.[51] SEQ ID NOS: 7-9 in Table 1 comprise the LHRH immunogen peptides and are useful in a vaccine for prostate cancer immunotherapy, designed for hormone ablation treatment. SEQ ID NOS: 10-11 are useful in an anti-IgE immunotherapeutic vaccine for the treatment of allergy. SEQ ID NOS: 4-6 are useful in an anti-CD4 immunotherapeutic vaccine for the treatment of HIV infection.

The Immunostimulatory complex of the present invention may be prepared with various ratios of cationic peptides to CpG oligonucleotides to provide different physical properties, such as the size of the microparticulate complexes. Table 2 shows the calculated average molar positive charge and calculated average peptide immunogen in the mixture. Table 2 also provides the calculated average molar negative charge contribution from CpG1 (SEQ ID NO: 1) and CpG2 (SEQ ID NO: 2), respectively.

Example 1

Preparation of Immunostimulatory Complex of LHRH Immunogens and CpG1 Oligonucleotides This Example illustrates the preparation of immunostimulatory complex from LHRH peptide immunogens and CpG1 oligonucleotides in various proportions. A flow diagram of the process of complex formation as described herein is shown in FIG. 1.

All glassware, stir bars and pipette tips were autoclaved for 40 minutes at 121° C. prior to use. All reagents were weighed, dispensed, transferred or added to reaction vessels in a laminar flow hood to prevent contamination.

An LHRH peptide immunogen stock solution was prepared by mixing a 1:1:1 molar ratio of peptides of SEQ ID NOS: 7-9 at a concentration of 3 mg/mL in distilled deionized water. 33 μL of the stock solution (100 μg of the peptide immunogens) was added to each of a series of 2 mL vials equipped with micro stir bars. To this solution was added 0.5 mL of distilled deionized water as a diluent. A stock solution of 2.0 μg/μL of CpG1 oligonucleotide was prepared in distilled deionized water. Various amount of the CpG1 oligonucleotide stock solution was added to each vial to form the immunostimulatory complex. The amount of CpG1 oligonucleotide added to each vial was in amount to provide a charge ratio of LHRH:CpG1 ranging from 8:1, with a large excess of LHRH, to 1:2 with an excess of CpG1. The respective amounts of CpG1 used to prepare these compositions are shown in Table 3. It is to be noted that the ratio of LHRH:CpG1 are in charge ratios and is based on the calculation of the average charge ratio also shown in Table 3.

The additions were made at room temperature with continuous stirring and equilibrated for 30 min. In all cases, an immediate clouding of the reaction mixture was observed upon addition of the CpG oligonucleotide stock solution. After complete addition of the CpG1 oligonucleotide, a fine white particulate suspension was observed. The particles gradually settled and could be easily re-suspended with gentle shaking.

The solid microparticulate complexes can be essentially removed after settling and allow the supernatant solutions to be analyzed by ultraviolet spectroscopy for residual uncomplexed peptide immunogens (at λ=280 nm) or for residual CpG1 oligonucleotide (at λ=260 nm). For the immunostimulatory complexes prepared using an excess of LHRH, wherein LHRH:CpG1=8:1, 4:1 or 2:1, excess amounts of peptide were detected.

The result obtained is an estimate and may be ±20% of the number obtained for the following reasons. The peptide chromophores have sizeably smaller extinction coefficients as compared to CpG oligonucleotides and the wavelength maxima used to detect the peptides and CpG1 are fairly close to each other. Thus, the estimates for free residual peptide may possibly be exaggerated. Further, a small amount of nanoparticles of peptide CpG complex may be present in the supernatant. The interpretation of these results is further complicated by the observation that increasing the excess amount of the peptide immunogen relative to CpG generally results in complex aggregates with smaller average particle sizes.

Figure 2:
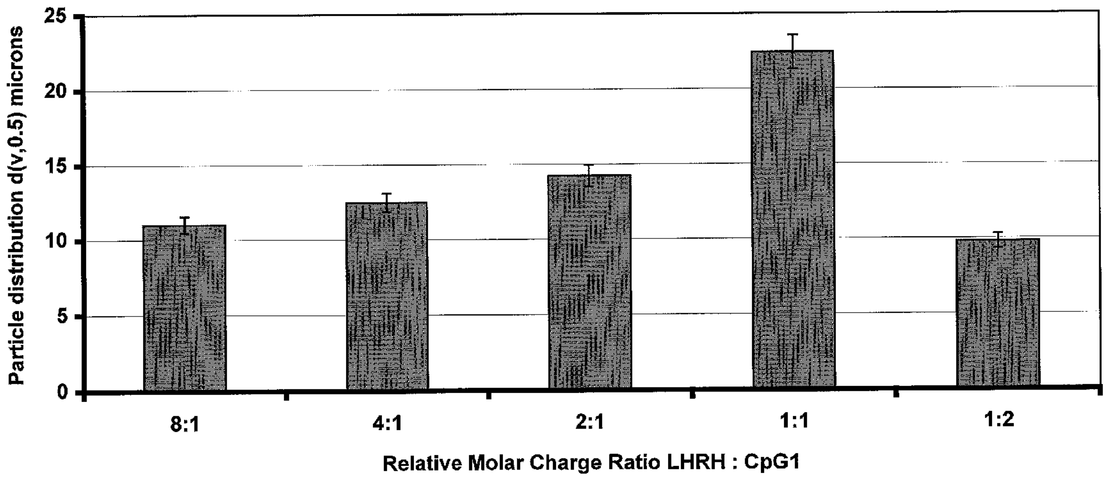
FIG. 2 shows the typical size distribution for the stabilized immunostimulatory complexes prepared from LHRH peptide immunogens and CpG1 oligonucleotides in various proportions as determined by laser diffraction measurements.

It is observable from FIG. 2 that the ranking of LHRH/CpG1 complexes with respect to average particle size distribution is in the order LHRH:CpG1 2:1>4:1>8:1. It is expected that the efficiency of the complexation process would vary based on the physical properties of the peptide immunogens and CpG oligonucleotides selected and the relative ratio of each in the vaccine composition. For the LHRH:CpG1 system, the residual levels of uncomplexed peptide as determined by UV spectroscopy range from 60-90% (LHRH:CpG1=8:1), 40-80% (LHRH:CpG1=4:1) and 25-65% LHRH:CpG1=2:1) over the background, respectively. For the LHRH:CpG1 complex prepared at a 1:1 charge ratio there was very little detectable concentration of residual peptide immunogen, ~3%, or residual CpG oligonucleotide, ~2%. The large increase in the aggregate size of this complex coupled with the essentially complete complexation of immunogen is consistent with polyelectrolytes reactions at neutral charge. For the immunostimulatory complex LHRH:CpG1=1:2 charge ratio, an excess of CpG1, 48% residual level of CpG1 was found at λ=260 nm. This amount of residual CpG1 approximates the quantity of CpG1 expected if the first equivalent of CpG1 was fully complexed with the peptide immunogen in solution.

This demonstrates that immunostimulatory complex compositions prepared with a high excess of peptide to oligonucleotide (e.g. LHRH:CpG1=8:1 charge ratio) results in a significant amount of peptide free in solution. Similarly, immunostimulatory complexes prepared from a moderate excess of oligonucleotide to peptide (e.g. LHRH:CpG1=1:2 charge ratio) result in compositions with excess free oligonucleotide. The presence of excess oligonucleotide can serve to stabilize smaller aggregates as shown in FIG. 2, Example 1.

This example demonstrates that there may be no practical advantages to preparing immunostimulatory complex with a high excess of LHRH, LHRH:CpG1=8:1 charge ratio, wherein a significant amount of peptide remain free in solution. Similarly, there is no practical advantage for immunostimulatory complex prepared with a moderate excess of CpG1, LHRH:CpG1=1:2 charge ratio, wherein it is reasonable to assume that after complete complexation at the point of electrical neutrality, excess oligonucleotide can serve only to stabilize smaller aggregates as shown in FIG. 2 and Example 1. This result does reveal that compatible anionic molecules and/or polymers may be sequentially added to a preformed 1:1 electrically neutral complex in order to reduce the effective particle size of the composition. This presents a novel strategy for complete immunostimulatory complexation coupled with particle size control.

It is an object of this invention to effectively bind the peptide immunogens in solution for certain applications to maximizing the potential stability of the vaccine in vivo. Thus immunostimulatory complex prepared with charge ratios of peptide immunogens to CpG oligonucleotides ranging from 4:1 to 1:1 respectively are preferred. It is another object of this invention to maximize the adjuvanticity of the immunostimulatory complex in vivo by using smaller more discrete particles (~10 microns or less) for presentation to the immune system.

It has been found that the presence of residual free and uncomplexed peptide is more desirable for more complex vaccine formulations such as water-in-oil emulsions or absorption on to mineral salts. In these formulations, adjuvantation of the immune responses may result from immunogens bound as immunostimulatory complex and also from uncomplexed immunogens dispersed within the w/o emulsion or adsorbed on the mineral salt directly. Thus, the immunostimulatory complexes prepared with charge ratios of peptide immunogens to CpG oligonucleotides ranging from 8:1 to 2:1 are found to be useful for these applications.

More preferably, a combination of maximal peptide complexation for stability and small particle size for improved adjuvanticity is found for immunostimulatory complexes prepared with charge ratios of peptide immunogens to CpG oligonucleotides ranging from 4:1 to 2:1.

The most preferred immunostimulatory complex are those prepared to possess physical properties, which make them suitable for alternative delivery modalities. Specifically, average particle sizes on the order of 10 microns or less are desirable in particular for rectal, vaginal, oral and nasal delivery.

Example 3

Preparation of Dried Immunostimulatory Complex

This Example illustrates the procedure used to prepare an immunostimulatory complex in a dry state.

Suspensions of LHRH/CpG1 complexes, prepared as described in Example 1, in 0.5-1.0 mL in aqueous solvent, distilled deionized water, normal saline or phosphate buffered saline, were placed in a dry ice/acetone bath and frozen for 15 minutes. The frozen samples were then placed on a freeze-dryer (Vertis 25LEZ) and the water removed by sublimation at 200 millitorr over three days. This procedure provided a near transparent glassy finished product in the vial. The appearance of the residual solid recovered depends on the aqueous solvent used and can range from a near transparent glass to a white fluffy solid.

Reconstitution of the dried materials in the same volume of aqueous solvent regenerated a suspension of discrete particles. The particle size distributions, determined as described in Example 2, showed essentially no change.

This demonstrated that the drying and resuspension process does not effect the physical properties of the prepared immunostimulatory complexes. Thus, a vaccine composition comprising the immunostimulatory complexes of the present invention may be provided in the form of a suspension, a solid or a dried powder.

Example 4a

Preparation of Water-in-Oil Emulsions Using High Shear Homogenization

Figure 3:
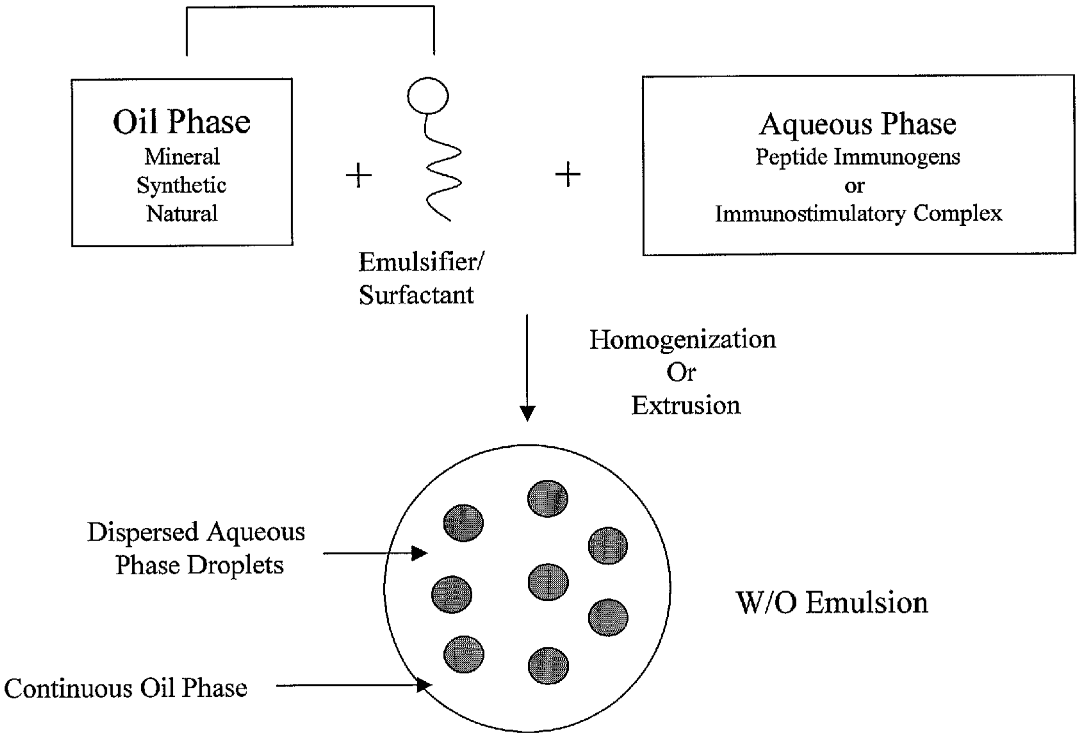
FIG. 3 is a schematic of the process for preparing a water-in-oil (w/o) emulsion employing homogenization or extrusion techniques.

This Example illustrates the process of preparing a water-in-oil (w/o)-emulsion from cationic peptides derived from LHRH peptide immunogens (SEQ ID NOS: 7-9 in a 1:1:1 molar ratio in solution), IgE peptide immunogens (SEQ ID NO: 10-11 in a 2:1 molar ratio in solution) CD4 peptide immunogens (SEQ ID No: 4-6 in a 2:1:1 molar ratio in solution) or immunostimulatory complex derived from LHRH, IgE or CD4 immunogens and CpG1 or CpG2 oligonucleotides in various proportions using homogenization techniques. A flow diagram illustrating the process of emulsion formation via homogenization as described herein is shown in FIG. 3.

All glassware, stir bars and pipette tips were autoclaved for 40 minutes at 121° C. prior to use. All reagents were weighed, dispensed, transferred or added to reaction vessels in a laminar flow hood to prevent contamination.

The w/o-emulsions were optimized for stability with respect to the volume ratio of the aqueous to oil phases required. For compositions employing Montanide® ISA 720 oils (SEPPIC, Inc) the ratio of water to oil was 30:70 by weight. For compositions employing ISA Montanide® 51 oils (SEPPIC, Inc.) the ratio of water to oil was 50:50 by weight.

Example 4b

Preparation of Water-in-Oil Emulsions from ISA Montanide® 720 and Immunostimulatory Complex To a 10 mL vessel, was added 3,333 μg of peptide immunogens dissolved in an appropriate aqueous buffer (1,111 μL, 3 mg/mL) or an immunostimulatory complex prepared from 3,333 μg of peptide immunogens dissolved in an appropriate aqueous buffer (1,111 μL, 3 mg/mL) and either CpG1 or CpG2 oligonucleotides. Table 3 and Table 4, shows the calculations for determining relative amounts of each reagent employed.

Specifically, to prepare an immunostimulatory complex from LHRH peptide immunogens at a 4:1 charge ratio of LHRH:CpG1, 244 μg CpG1 oligonucleotide (122 μL, 2.0 μg/mL) were used.

Specifically, to prepare an immunostimulatory complex of IgE peptide immunogens at a 4:1 charge ratio of IgE:CpG1, 387 μg of CpG1 oligonucleotide (193.5 μL, 2.0 μg/μL) were used. To form a 1:1 neutral complex of IgE:CpG1, 1,548 μg of CpG1 oligonucleotide (774.0 μL, 2.0 μg/μL) were used.

Specifically, to prepare an immunostimulatory complex of CD4 peptide immunogens at a 2:1 charge ratio of CD4:CpG2, 402 μg of CpG2 oligonucleotide (201 μL, 2.0 μg/μL) were used. To form a 1:2 charge ratio of CD4:CpG2, 1608 μg of CpG2 oligonucleotide (804 μL, 2.0 μg/μL) were used.

To each of the vessels additional diluent aqueous solvent was added so that the final volume of the aqueous phase was fixed at 3.0 mL for preparation of ISA Montanide® 720 w/o-emulsions respectively.

For LHRH or IgE peptides normal saline or PBS was found to be suitable for complexation. The calculated IP for each peptide immunogen is greater than 9.0 (Table 1), far greater than the pH of the aqueous solvent selected.

In the case of CD4 peptides the choice of aqueous solvent proved important. Upon dilution with either normal saline or PBS a solid precipitate was observed to quickly form in solution. This instability would preclude use of this immunogen combination by parenteral routes. An examination of the peptide immunogens revealed that peptide sequence ID No: 6 (Table 1) has a calculated ionization point of 6.91. In PBS (pH ~7.2), this peptide would tend to aggregate and be expected to exhibit instability. A solution to this problem was found by first preparing the immunostimulatory complex in distilled deionized water followed by dilution with saline or PBS of sufficient ionic strength to ensure that the suspension was isotonic and suitable for injection.

This example demonstrates the advantages of stabilizing immunogens in solution in the form of an immunostimulatory complex of LHRH, IgE or CD4 peptides.

The diluted aqueous solutions or suspensions were then slowly added to a dry 25 mL reaction vessel charged with 7.0 gm of ISA Montanide® 720 (8.1 mL, 0.86 gm/mL). The additions were made while homogenizing (High Shear Laboratory Mixer, Sealed Unit, Silverson) the mixture at low speeds (2,000-3,000 rpm) to generate a coarse emulsion. This processing speed was maintained until the aqueous sample had been completely added and was continued a full 2 minutes to ensure uniform pre-mixing of the aqueous and oil phases. The homogenization speed was then ramped up (5,000-8,000 rpm) and maintained for from 5 to 10 minutes further resulting in the formation of a homogeneous white finely dispersed w/o-emulsion.

The final concentration of immunogens once formulated as suspensions or in water-in-oil emulsions as described above was 200 μg/mL.

Example 4c

Stability Evaluation for Water-in-Oil Emulsions Prepared by Homogenization Methods The consistency and stability of the w/o-emulsions prepared by homogenization was checked by a variety of methods. To prove that the emulsion was water-in-oil (w/o) and not oil-in-water (o/w) or water-in-oil-in-water (w/o/w), a droplet of the composition was added to a beaker containing distilled deionized water. A droplet of a w/o-emulsion will float on the surface and not disperse into water. Conversely, a droplet from an o/w emulsion will instantly disperse into water and a droplet from a w/o/w double emulsion will disperse both on the surface and into the bulk of the aqueous phase. Droplets from the emulsions prepared from ISA Montanide® 720 were observed to float on the surface with minimal dispersal and droplets from the emulsions prepared from ISA Montanide® 51 oils were observed to float on the surface with essentially no dispersal. These results indicated that the emulsions were w/o and further that the tendency towards dispersal was higher for the w/o-emulsion prepared from ISA Montanide® 720. This is related to the initial viscosity of the oils themselves and the viscosity of the resultant emulsions. This is an important consideration for maximizing the depot potential of the resultant vaccine formulation.

The apparent viscosity of the finished emulsions and oils were checked (Brookfield DV-1+ rotational viscometer) for lot to lot consistency and for long-term stability trials. ISA Montanide® 720 had a viscosity of ~15 mPa at 25° C. whereas the w/o emulsion prepared from ISA Montanide® 720 had a viscosity of ~45-50 mPa at 25° C. This provided a fairly fluid product, which is desirable for facilitating the handling, and dispensing of the vaccine with a syringe.

In contrast, ISA Montanide® 51 had a viscosity of ~50 mPa at 20° C. whereas the w/o-emulsions prepared from ISA Montanide® had a viscosity of ~1,500-2,900 mPa at 25° C. The wide variation in viscosity was found to be a function of buffer selection. (PBS=~2,900 mPa, NS=~2,500 mPa and distilled deionized water=~1,500 mPa) Material of this high viscosity can present some difficulties with respect to transferring and dispensing with a syringe. However, the long-term stability of these compositions was improved. The long-term stability of the emulsion was evaluated by placing 1 mL of each emulsion in a 1.5 mL eppendorf vial and centrifuging the contents under high speed (5,000 rpm) for 10 minutes. These conditions do not simulate actual storage conditions but can be used to predict the resistance of the emulsion to separation. In the case of ISA Montanide® 720, 5-10% of the volume separated out with a clear or straw yellow oil phase observed on the surface. In the case of ISA Montanide® 51, 0-2% of the volume separated out with a clear or straw yellow oil phase observed on the surface. The higher viscosity of the ISA Montanide® 51 emulsion products accounts for the greater stability to sedimentation and resistance to separation.

Figure 4:
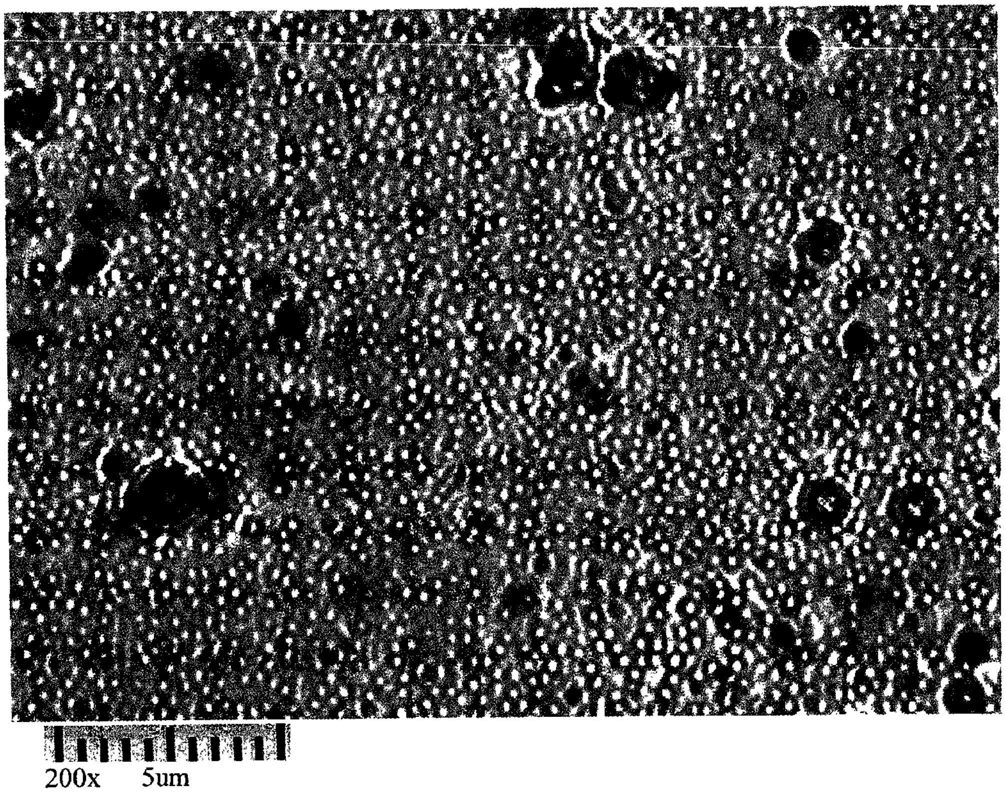
FIG. 4 shows a typical photomicrograph for a w/o emulsion prepared via homogenization from ISA Montanide® 51 and LHRH:CpG1 immunostimulatory complexes, wherein LHRH:CpG1 is 4:1 at a fixed final total peptide concentration of 100 μg/mL.

The particle size and distribution for the w/o-emulsion was further characterized by optical microscopy (Nikon DIAPHOT 200). A photomicrograph of each composition was obtained and an estimate of the size range of particles was made using a computer-generated scale. The scale itself is externally referenced against standards of known particle sizes (NIST traceable microparticles—Duke Scientific). For w/o emulsions prepared from either ISA Montanide® 720 or ISA Montanide® 51 and peptide immunogens, the particles sizes were essentially the same (c.a. 1-2 microns) with minimal aggregation or coalescence. For w/o-emulsions prepared from either ISA Montanide® 720 or ISA Montanide® 51 and immunostimulatory complex the particle sizes were slightly larger (c.a. 1-3 microns) with minimal aggregation or coalescence. FIG. 4 is a photomicrograph obtained from a w/o-emulsion prepared via homogenization from ISA Montanide® 51 and an immunostimulatory complex derived from 100 μg of the LHRH peptide immunogens, with LHRH:CpG1 in a final charge ratio of 4:1.

The initial average particle size was on the order of 10 microns. The process of homogenizing an aqueous suspension of immunostimulatory complexes under high shear resulted in a smaller average aggregate particle size. A stable w/o-emulsion with droplets in the size in the range of 1-3 microns was obtained.

Example 5a

General Preparation of Water-in-Oil Emulsions Using Low Shear Extrusion

This Example illustrates the process of w/o-emulsion formation from cationic peptides derived from LHRH, IgE or CD4 immunogens or immunostimulatory complex derived from LHRH, IgE or CD4 immunogens and CpG1 or CpG2 oligonucleotides in various proportions using extrusion techniques. Table 3 and Table 4, shows the general calculations for determining the relative amounts of each reagent employed. A flow diagram illustrating the process of emulsion formation via extrusion as described herein is shown in FIG. 3.

All glassware, stir bars and pipette tips and the entire extruder mechanism were autoclaved for 40 minutes at 121° C. prior to use. All reagents were weighed, dispensed, transferred or added to reaction vessels in a laminar flow hood to prevent contamination.

The extrusion process involves repeatedly passing an aqueous phase loaded in one syringe into an oil phase loaded in a second syringe through a narrow bore tube joining the two syringes. Emulsification occurs as the fluids are driven through the narrow bore under pressure, typically 100 psi. By contrast, a homogenizer system typically operates at a pressure that is greater than 1,000 psi. The number of return passages necessary for the above extrusion process often exceeds 20 to 30 before a visually uniform w/o-emulsion is generated. This manual extrusion process cannot generate significant shear and the number of exchanges required to efficiently produce a w/o-emulsion is highly variable. The physical properties of the w/o-emulsions are inconsistent and the overall stability and consequently in vivo potency are typically highly irreproducible. In spite of these problems, there are a number of possible applications for products produced by this process.

To address these shortcomings an extruder mechanism has been developed (LiposoFast™ Basic, Avestin, Inc., Ottawa, Canada). The device consists of two syringes (0.5 mL or 1.0 mL) fitted via luer locks with a narrow bore passage connected to a holder with a polycarbonate membrane of a defined pore size placed in between the two syringes. The device as originally designed was for the preparation of liposomes of a controlled size.[63] The application of such a device with a compatible oil-based product for the preparation of w/o emulsions appears not to have been contemplated. The membrane pore size can be selected (Whatman Nucleopore, 0.05 μM-10 μM). The smaller pore size allows for the extrusion of dispersions under increased shear. The larger pore size can be selected for formulating wherein the particulates are larger sized. Using this device, the efficiency of emulsification was increased. Fewer return passages were required to provide a more uniform and stable product. The in vivo potency of such a preparation would be predicted to be more reproducible. However, there are still limitations due to the small maximum volume, c.a. 1.0 mL, which can be practically employed and the practical restrictions on the choice for the oil component.

The process works well for the preparation of w/o-emulsions derived from ISA Montanide® 720. However, the higher viscosities of emulsions derived from ISA Montanide® 51 results in significant backpressure, precluding the use of this extrusion device. As such, this method can be best viewed as a process for preparing instant w/o emulsions from oils with apparent viscosities of less than 1,500 mPa.

In particular, where the costs associated with storage and stability of vaccines are of concern or where patient compliance is an issue or application as a palliative medicine is involved, this method of delivery may be cost effective and practical. Ideally, trained practitioners such as doctors or pharmacists can be relied upon for preparing instant w/o-formulations on-site for general use.

This device and protocol may be used for the preparation of instantaneous o/w, and w/o/w, microemulsions for which controlled shear and extrusion are required, or for the preparation of refined products.

Example 5b

Preparation of Water-in-Oil Emulsions from ISA Montanide® 720

To a 1.0 mL glass syringe (gas tight), was added 333 μg of LHRH, IgE or CD4 peptide immunogens dissolved in an appropriate aqueous buffer (111 uL, 3 mg/mL) or an immunostimulatory complex (with a 4:1 charge ratio) prepared from 333 μg of LHRH or IgE peptide immunogens or an immunostimulatory complex (with a 2:1 charge ratio) prepared from 333 μg of CD4 peptide immunogens dissolved in an appropriate aqueous solvent (111 μL, 3 mg/mL) and CpG1 or CpG2 oligonucleotides in appropriate ratios as described in Tables 3 and Table 4, respectively.

Specifically, to prepare immunostimulatory complex from LHRH peptide immunogens at a charge ratio of LHRH:CpG1 of 4:1, 24.3 μg CpG1 oligonucleotide (12.2 μL, 2.0 μg/mL) were added.

To prepare immunostimulatory complex from IgE peptide immunogens at a charge ratio of IgE:CpG1 of 4:1, 38.7 μg of CpG1 oligonucleotide (19.4 μL, 2.0 μg/μL) were added or to form a 1:1 neutral complex of IgE:CpG1, 154.8 μg of CpG1 oligonucleotide (77.4 μL, 2.0 μg/μL) were added.

To prepare immunostimulatory complex from CD4 peptide immunogens at a charge ratio of CD4:CpG2 of 2:1, 40 μg of CpG2 oligonucleotide (20 μL, 2.0 μg/μL) were added or to form a complex at a charge ratio of CD4:CpG2 of 1:2, 160 μg of CpG2 oligonucleotide (80 μL, 2.0 μg/μL) were added.

Additional diluent aqueous solvent was added so that the final volume of the aqueous phase was 300 μL.

To a second 1.0 mL glass syringe (gas tight), was added 700 mg of ISA Montanide® 720. The syringes were connected via luer locks to an extrusion-housing unit containing a membrane holder and support for the polycarbonate membrane filter. Membrane filters with pore sizes 3 μM or 5 μM were selected for w/o-emulsions to be prepared with peptide immunogens in the aqueous phase. Whereas, membrane filters with pore sizes 5 μM or 10 μM were selected for the preparation of w/o emulsions with immunostimulatory complex suspended in the aqueous phase. The aqueous phase was then first passed through the membrane into the oil phase, typically with great ease. The subsequent exchanges require additional pressure with the increased backpressure generated during the emulsion process. After 8-12 passages the backpressure upon extrusion had equalized and a homogeneous white emulsion was typically obtained.

The final concentration of immunogens once formulated as solutions or as immunostimulatory complex in water-in-oil emulsions as described above was 200 μg/mL.

Example 5c

Stability Evaluation for Water-in-Oil Emulsions Prepared by Extrusion

Figure 5:
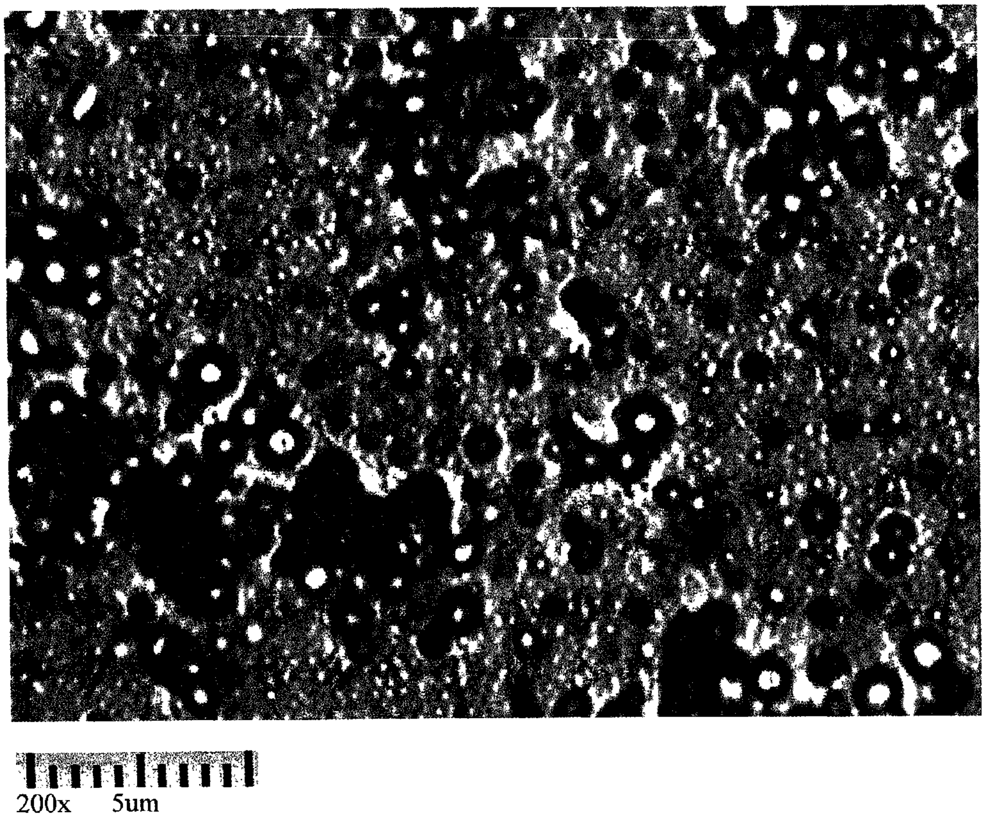
FIG. 5 shows a typical photomicrograph for a w/o emulsion prepared via extrusion from ISA Montanide® 720 and LHRH:CpG1 immunostimulatory complexes, wherein LHRH:CpG1 is 4:1, at a fixed final LHRH peptide concentration of 200 μg/mL.

Stability tests similar to those conducted in Example 4c, prepared by the extrusion processes confirmed that these compositions were w/o-emulsion. Droplets placed on the surface of distilled deionized water were observed to float with minimal dispersal. The viscosities of the resultant emulsions were found to range from ~35-40 mPa, a slight reduction when compared to the high energy homogenized system in Example 4c. The size distribution of the emulsion droplets was larger than the analogous homogenized systems. About 1-3 microns for w/o emulsions prepared from peptide immunogens or 2-5 microns for w/o emulsions prepared from immunostimulatory complex. For comparison, FIG. 5 is a photomicrograph obtained from a w/o emulsion sample prepared via extrusion from ISA Montanide® 720 and an immunostimulatory complex derived from 200 μg of LHRH peptide immunogens and CpG1 oligonucleotides in a final charge ratio of LHRH:CpG1 of 4:1. In general, the size of the droplets were larger as shown in FIG. 5. Overall, these instant w/o emulsions are sufficiently stable for immediate or same day use.

Example 6a

Preparation of In-Situ Polymeric Gels

Figure 6:
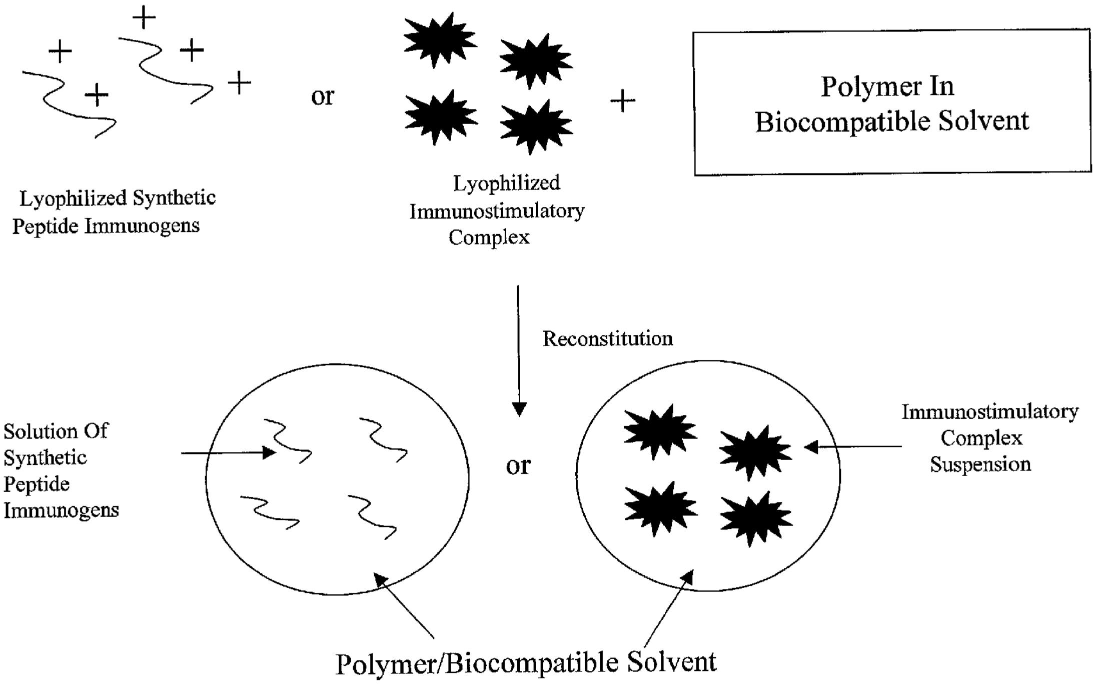
FIG. 6 is a schematic detailing the in-situ polymer gel process employing reconstitution.

This Example illustrates the process of in-situ gel matrix formation and encapsulation of immunostimulatory complex derived from IgE or CD4 immunogens and CpG1 or CpG2 oligonucleotides in various proportions using direct reconstitution techniques. A flow diagram showing the process of preparing an in-situ gel formulation with either peptide immunogens or immunostimulatory complex via reconstitution as described herein is shown in FIG. 6.

All glassware, stir bars and pipette tips were autoclaved for 40 minutes at 121° C. prior to use. All reagents were weighed, dispensed, transferred or added to reaction vessels in a laminar flow hood to prevent contamination.

In general, varying weight percentages of PLG or PLGA copolymers (Boehringer Ingelheim) were dissolved in biocompatible solvents such as anhydrous dimethyl sulfoxide (DMSO, Aldrich). The solubilization process required vigorous agitation for higher molecular weight polymers with continuous stirring maintained for from 4-6 hours to ensure complete dissolution. The polymer solution was then filtered through an organic solvent compatible membrane of pore size 0.45 microns (Phenomenex, PTFE). To this was added a solution of cationic peptide immunogens or more preferably a suspension of immunostimulatory complex in an appropriate biocompatible solvent. The peptide immunogen or peptide/CpG complex or a mixture thereof was first lyophilized (as described in Example 3) and subsequently dissolved or resuspended in an appropriate biocompatible solvent, such as DMSO.

The use of polar aprotic solvents, such as DMSO, may present some problems with respect to long-term peptide stability. DMSO is known as a powerful oxidizing agent, and peptides containing sensitive amino acids such as cysteine and tryptophan may be chemically incompatible in these solutions. Thus, peptide immunogens containing these residues may have to be reconstituted on site for immediate use.

The lyophilized peptide immunogens or immunostimulatory complex or a mixture thereof was reconstituted directly in the vial into a solution of polymer in DMSO at the time of use, thereby avoiding prolong exposure of the peptide immunogens to DMSO. The dissolution of the peptide immunogen or the resuspension of immunostimulatory complex or a mixture of the immunostimulatory complex with peptide immunogens was rapid, requiring gentle shaking to ensure sample uniformity.

There are minimal stability and manufacturing issues expected for these generic compositions. The polymer solutions in anhydrous DMSO are not as susceptible to hydrolytic degradation as compared with peptide immunogens dissolved or suspended in aqueous solutions. The polymer solution may be frozen (DMSO freezes at c.a. 18° C.) with no detectable changes in the physical properties upon thawing. The peptide or immunostimulatory complex isolated in the lyophilized dry state would also be expected to exhibit increased stability in the absence of water.

The mixture of polymer and peptide immunogens or immunostimulatory complex as such constitutes a single-phase solution or a suspension suitable for subcutaneous or intramuscular injection.

Of importance for either system is the viscosity of the solution or suspension. This directly influences the ability to syringe and inject the compositions by a subcutaneous or intramuscular route.

The apparent viscosity of these systems is a function of various factors including the constitution, molecular weight, crystallinity and intrinsic viscosity of the PLG or PLGA copolymers. These factors delimit the useful amount by weight for each polymer that can be dissolved while maintaining practical flow characteristics. Table 5 shows the physical properties for selected PLG or PLGA polymers and the corresponding amount in weight percentages that may be dissolved in DMSO to obtain solution viscosities of practical use. The apparent viscosity for these solutions was determined by a Brookfield DV-1+ rotational viscometer.

100 mPa was arbitrarily chosen as the upper desired limit for these compositions. In most cases a solution or suspension formulated as an in-situ gelling polymer solution with an apparent viscosity less than 200 mPa can be uniformly delivered through conventional syringes.

A polymer/DMSO solution with polymer to solvent in excess of that required to provide an apparent viscosity of 100 mPa would be of value for delivery by an alternative modality, including conventional syringe or a needleless method. The gelling behavior upon injection and burst release of the immunogen is in part related to the concentration of the polymer in the composition. Consequently, maximizing the rate of gellation and reducing the burst release of immunogen would be two additional design parameters for consideration in the development of an optional single-dose controlled release composition.

Example 6b

Preparation of Polymers Gels From PLGA Resomer® —RG 503H or RG 504H

To two separate 25 mL flasks equipped with stir bars was added 2,200 mg RG 504H or 2,750 mg RG 503H respectively. To each flask was added 10.0 mL of anhydrous DMSO (1.1 gm/mL) by transfer pipette. The mixtures were vigorously stirred for c.a. 2-3 hours at room temperature after which the copolymers were fully solubilized. After complete dissolution the stock solutions were filtered through a 0.45 μM organic solvent stable membrane filter (Phenomenex, PTFE). The final weight percent of RG 504H and RG 503H polymer to DMSO solvent was 20% and 25% respectively.

10 mL of the polymer/DMSO solution so prepared was then added via syringe into vials containing lyophilized IgE or CD4 peptide immunogens (2,000 μg) or lyophilized immunostimulatory complex (4:1 IgE:CpG1 charge ratio or 2:1 CD4:CpG2 charge ratio) derived from 2,000 μg of IgE peptides mixed with 232 μg of CpG1 oligonucleotide (116 μL, 2.0 μg/μL) or 2,000 μg of CD4 peptides mixed with 241 μg of CpG2 oligonucleotide (120.5 μL, 2.0 μg/μL). The final concentration of immunogen in solution or in the form of an immunostimulatory complex in suspension was 200 μg/mL. The immunogen or immunostimulatory complex was immediately reconstituted in solution or suspension with gentle shaking to ensure content uniformity.

The apparent viscosities of the solutions prepared from these polymers at the specified weight ratios were found to be close to 100 mPa. (see Table 5). The concentrations for Resomer® RG 503H, Resomer® RG 504H and Resomer® RG 756 for a solution viscosity of around 100 mPa were critical, Resomer® RG 503H and Resomer® RG 504H have much lower inherent viscosities and both are derived from PLGA with amorphous character, wherein the monomer composition was around 50% D,L-lactide and 50% glycolide. These materials would be expected to degrade at a rate of 6-8 weeks for 50% of the polymer in vivo. Thus, the encapsulated components would have a two-three month release profile with gels prepared from Resomer® RG 503H or Resomer® RG 504H. Gels prepared from these materials would be most suited for short-term single-dose controlled release applications. Conversely, Resomer® RG 756 is a more crystalline polymer composed of 75% D,L-lactide to 25% glycolide residues. It may require from 4-6 months for 50% of the polymer to degrade in vivo and the release rate for encapsulated components would consequently be more protracted. Resomer® RG 756 would be expected to be more desirable for long-term single-dose controlled release applications.

Example 7

The Immunogenicity of IgE and CD4 Peptide Immunogens Formulated as Immunostimulatory Complex or as W/O Emulsion or in Combinations This Example illustrates the immunogenicity of IgE and CD4 peptide immunogens formulated as immunostimulatory complexes with CpG1 or CpG2 oligonucleotides, as a w/o-emulsion or as immunostimulatory complex dispersed in a w/o-emulsion in guinea pigs, which were immunized intramuscularly. The w/o-emulsions were prepared by homogenization as described in Example 4a/4b or by extrusion as described in Example 5a/5b.

Groups of three, 6 to 8 week old female guinea pigs (Covance Research Products Inc., Denver, Pa.) were immunized intramuscularly (I.M.) on week 0, 3 and 6 with following compositions: 100 μg of the IgE peptides/CpG1 immunostimulatory complex (2:1 charge ratio and 1:2 charge ratio) prepared as described in Table 4 was suspended in a final volume of 250 μL PBS, pH 7.4; IgE peptides was emulsified in 75 μL PBS, pH 7.4 with ISA Montanide® 720 (175 μL). CD4 peptides in 75 μL distilled deionized water was emulsified with ISA Montanide® 720 (175 μL). IgE peptide/CpG1 immunostimulatory complex in 75 μL PBS, pH 7.4 prepared as described in Table 4 (4:1 charge ratio and 1:1 neutral charge ratio) was emulsified with ISA Montanide® 720 (175 μL) of CD4 peptides/CpG2 immunostimulatory complexes prepared as described in Table 4 in 75 μL distilled deionized water (2:1 charge ratio and 1:2 charge ratio) was emulsified with ISA Montanide® 720 (175 μL).

The guinea pigs showed no gross pathologies or behavioral changes after receiving immunostimulatory complex, w/o emulsions containing peptide immunogens or w/o emulsions containing the immunostimulatory complex. Sera were obtained on weeks +3, +5, +9, +11 and +17 and were evaluated for the presence of anti-IgE antibodies in the case of IgE immunogens or anti-CD4 antibodies in the case of CD4 immunogens, by immunogen-specific ELISAS.

Measurement of Anti-IgE Antibodies

Anti-IgE peptide titers were determined by IgE peptide ELISA and cross-reactivities to human IgE by human IgE ELISA. Peptide ELISAs for determination of anti-IgE peptide reactivity were conducted in microtiter plates coated with the target antigen site peptide without the T helper site, as described[64]. For determination of anti-human IgE cross-reactivity, human IgE ELISAs were conducted in microtiter plates coated in a likewise fashion with a human IgE myeloma protein (American Biosystems, Inc. cat. no. A113) at 5 μg/ml. Captured anti-peptide or anti-IgE antibodies were detected by horseradish peroxidase-labeled anti-guinea pig IgG goat antibody. ELISA titers, expressed as $\log_{10}$ of reciprocal dilution, were calculated based on linear regression analysis of the absorbances, with cutoff $A_{492}$ set at 0.5. This cutoff value was rigorous as the values for diluted normal guinea pig control samples run with each assay were less than 0.15. Hyperimmune guinea pig anti-IgE peptide immunogen antiserum was used as a positive control. Pre-immune sera were used as negative controls.

Measurement of Anti-CD4 Antibodies

ELISAs for binding to recombinant soluble CD4 were done in 96 well microtiter plates coated with rsCD4 (American Bio-Technologies) at 0.25 μg/mL, using 100 μL per well in 10 mM $NaHCO_3$ buffer, pH 9.5. Wells were blocked with 250 μL of 3% gelatin, washed with 0.05% TWEEN 20 in phosphate-buffered-saline (PBS) and dried. Test wells were reacted with 100 μL of diluted immune sera for 1 hour at 37 C. Wells were washed with 0.05% TWEEN 20 in PBS, reacted with 100 μL of horseradish peroxidase-labeled goat anti-mouse IgG (Pierce) diluted 1:1000 in 1% goat serum, 0.05% TWEEN® 20 in PBS, and washed. 100 μL of orthophenylenediamine (OPD) substrate at 0.04% by weight (Pierce) and 0.12% $H_2O_2$ in sodium citrate buffer, pH 5.0, was added for 15 minutes. Reactions were stopped by addition of 100 μL 1.0 M $H_2SO_4$ and $A_{492}$ determined. Hyperimmune guinea pig anti-CD4 peptide immunogen antiserum was used as a positive control. Pre-immune sera were used as negative control.

Measurement of Functional Antigenicity by Competitive ELISA

In this competitive ELISA, functional antigenicity was quantitated for CD4 immunogens by testing the evoked antibodies for the capacity to competitively inhibit a functional monoclonal antibody, mAb B4, whose known specificity was for the CD4 complex on the host cell surface that binds HIV. This anti-binding site monoclonal antibody has been well-characterized for its high affinity for the HIV binding complex, for binding to domain 1 of soluble recombinant CD4 (rsCD4), and for its ability to neutralize HIV-1 primary isolates.[65]

The anti-binding site monoclonal antibody was purified by protein A affinity chromatography and conjugated to horseradish peroxidase. The mAb B4-HRP conjugate was used in the assay as a tracer, at a concentration of 0.5 μg/ml. 96-well microtiter plates were coated with recombinant soluble CD4 protein, 1 μg/ml in 0.1 M sodium carbonate buffer, pH 9.5, with overnight incubation. Reactions were done in the microtiter wells in 100 μl total volume of PBS/goat serum/gelatin/TWEEN® 20, with serially diluted immune serum (guinea pig, swine, or baboon) and 30 μl of the mAb B4-HRP working stock. Diluted serum and mab B4-HRP were pre-incubated prior to adding the mixture to the well. The positive control for the competition ELISA was 5 μl of unlabelled-anti-binding site mAb at 0.5 μg/ml in normal serum, the negative control is normal serum. The serum/antibody dilution mixture, 100 μl was added to a coated well and incubated for one hour at 37°. The plates were drained and washed and bound mAb B4-HRP was detected by reaction with a chromogen. The chromogen was 3,3',5,5'-tetramethylbenzidine (TMB) and TMB-bound mAbB4 conjugate was detected at $A_{450}$. A calibration curve was obtained with purified mAb B4 serially diluted from 10 μg/ml into normal serum of the appropriate species so as to obtain an mAb equivalent value for the dilutions of immune sera which competitively inhibit the binding to human recombinant soluble CD4 of the mAb B4-HRP.

Virus Neutralization Assay

The MT-2 microplaque assay was carried out as described[66] except that heat-inactivated sera were serially diluted in 50% high glucose DMEM with 15% FBS, antibiotics, 2% glutamine and bicarbonate buffer, and 50% pooled, defibrinated normal human plasma. In this assay, diluted serum is incubated with 20 pfu of HIV in microtiter wells. HIV-sensitive MT-2 cells are added and formed into monolayers by centrifugal force under molten agarose. Residual virus infectivity is detected by the presence of propidium iodide-stained plaques one week later. The endpoint is the serum dilution at which there was a 50% or 90% reduction in the plaque count.

Immunogenicity Results

Figure 7:
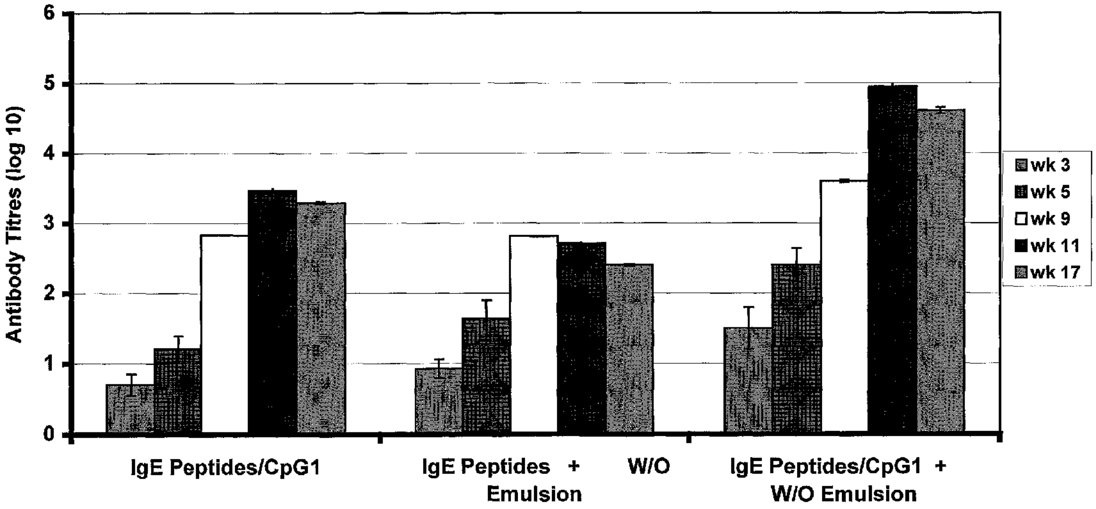
FIG. 7 shows the serum IgG responses in guinea pigs immunized intramuscularly (I.M.) in accordance with the following immunization protocols. Groups of 3 guinea pigs were immunized on weeks 0, 3 and 6 with three different preparations: 100 μg of an immunostimulatory complex of IgE peptides and CpG1 oligonucleotides suspended in 250 μL of PBS, pH 7.4; 100 μg of IgE peptides formulated as a w/o emulsion in 250 μL dose volume; or 100 μg of an immunostimulatory complex of IgE peptides and CpG1 oligonucleotides formulated as a w/o emulsion in 250 μL dose volume. The w/o emulsions were prepared by conventional homogenization. Sera obtained on week +3, +5, +9, +11 and +17 were evaluated for the presence of anti-IgE peptide antibodies using an enzyme-linked immunosorbent assay (ELISA).
Figure 8:
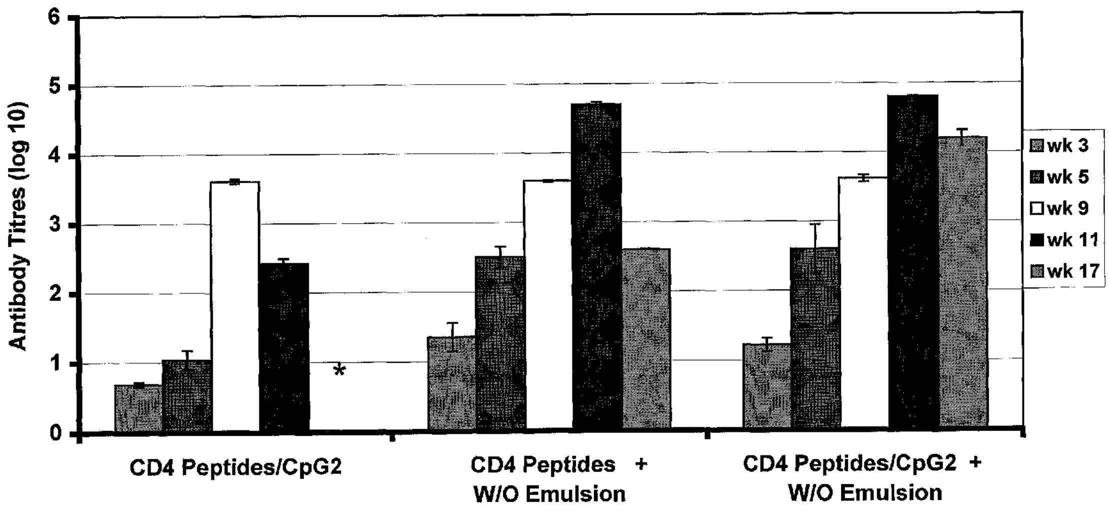
FIG. 8 shows the serum IgG responses in guinea pigs immunized intramuscularly (I.M.) in accordance with the following immunization protocols. Groups of 3 guinea pigs were immunized on weeks 0, 3 and 6 with three different preparations: 100 μg of an immunostimulatory complex of CD4 peptides and CpG2 oligonucleotides suspended in 250 μL of PBS, pH 7.4, 100 μg of CD4 peptides formulated as a w/o emulsion in 250 μL dose volume; or 100 μg of an immunostimulatory complex of CD4 peptides and CpG2 oligonucleotides formulated as a w/o emulsion in 250 μL dose volume. The w/o emulsions were prepared by conventional homogenization. Sera obtained on weeks +3, +5, +9, +11 and +17 were evaluated for the presence of anti-CD4 peptide antibodies using an enzyme-linked immunosorbent assay (ELISA). No sera were obtained for the animals immunized with the immunostimulatory complex derived from CD4 peptides and CpG2 on week 17. This is indicated by an asterisk in FIG. 8.
Figure 9:
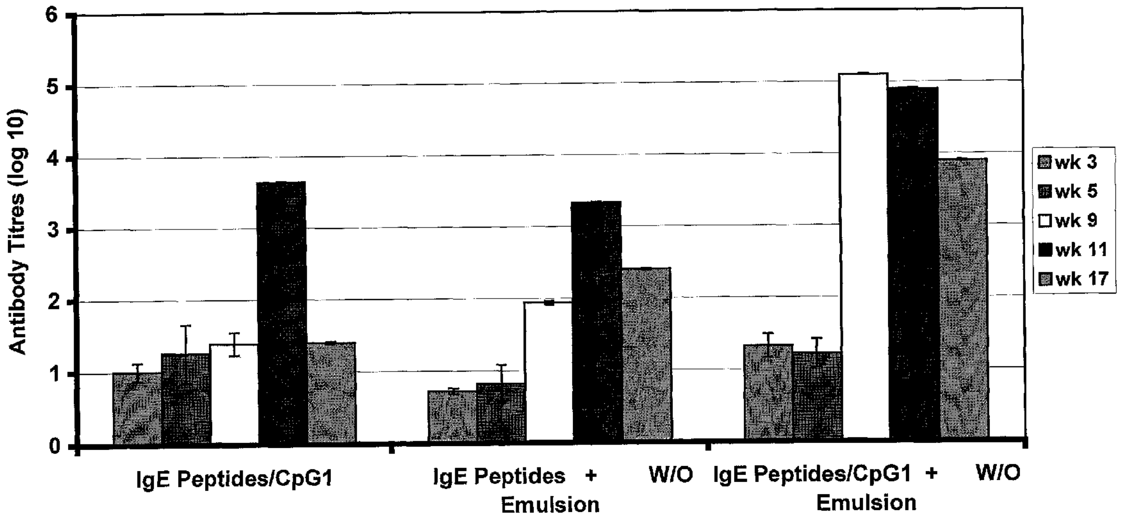
FIG. 9 shows the serum IgG responses in guinea pigs immunized intramuscularly (I.M.) in accordance with the following various immunization protocols. Groups of 3 guinea pigs were immunized on weeks 0, 3 and 6 with three difference preparations: 100 μg of an immunostimulatory complex of IgE peptides and CpG1 oligonucleotides suspended in 250 μL of PBS, pH 7.4; 100 μg of IgE peptides formulated as a w/o emulsion in 250 μL dose volume; or 100 μg of an immunostimulatory complex of IgE peptides and CpG1 oligonucleotides formulated as a w/o emulsion in 250 μL dose volume. The w/o emulsions were prepared instantaneously via extrusion. Sera obtained on week +3, +5, +9, +11 and +17 were evaluated for the presence of anti-IgE peptide antibodies using an enzyme-linked immunosorbent assay (ELISA).
Figure 10:
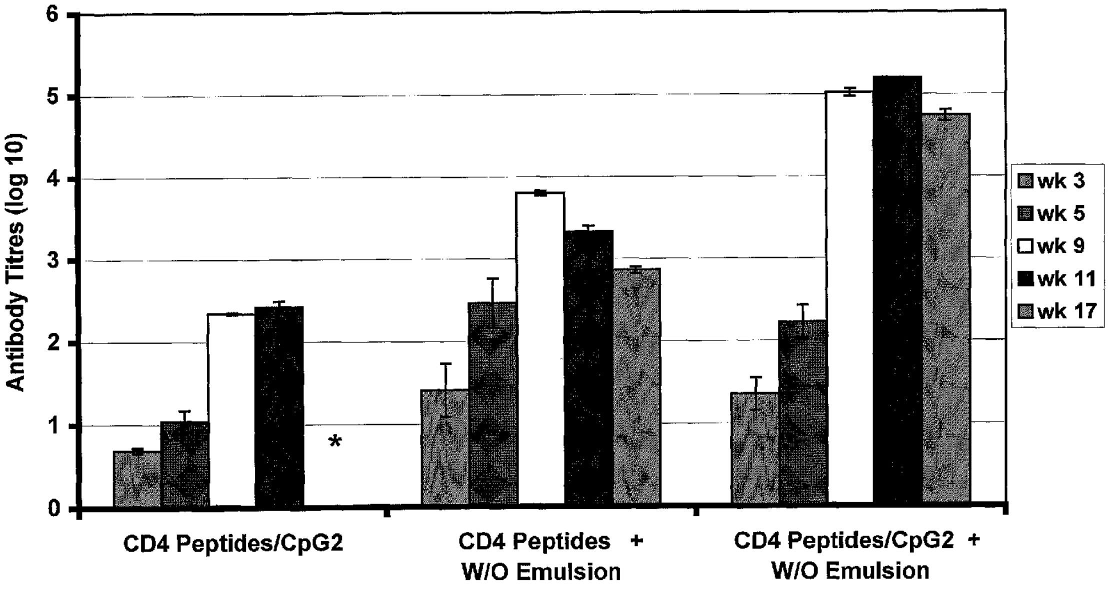
FIG. 10 shows the serum IgG responses in guinea pigs immunized intramuscularly (I.M.) in accordance with the following immunization protocols. Groups of 3 guinea pigs were immunized on weeks 0, 3 and 6 with three different preparations: 100 μg of an immunostimulatory complex of CD4 peptides and CpG2 oligonucleotides suspended in 250 μL of PBS, pH 7.4; 100 μg of CD4 peptides formulated as a w/o emulsion in 250 μL dose volume or 100 μg of an immunostimulatory complex derived from a cocktail of CD4 peptides and CpG2 oligonucleotides formulated as a w/o emulsion in 250 μL dose volume. The w/o emulsions were prepared instantaneously via extrusion. Sera obtained on weeks +3, +5, +9, +11 and +17 were evaluated for the presence of anti-CD4 peptide antibodies using an enzyme-linked immunosorbent assay (ELISA). No sera were obtained for the animals immunized with the immunostimulatory complex derived from CD4 peptides and CpG2 on week 17. This is indicated by an asterisk in FIG. 10.

The serum antibody titers following immunization of IgE immunogens are shown in FIG. 7 (homogenized systems) and FIG. 9 (extruded systems) and for CD4 immunogens are shown in FIG. 8 (homogenized systems) and FIG. 10 (extruded systems). Table 6 compares the competitive inhibition of a B4 monoclonal antibody assayed on sera obtained from the CD4 peptide study (homogenized and extruded w/o emulsion systems) on week 9, week 11 and week 17, respectively. Table 7 compares virus neutralization activity (50% and 90% inhibition respectively) assayed on sera obtained from the CD4 peptide study (homogenized and extruded w/o emulsion systems) on week 9 and week 11, respectively. Control experiments demonstrated that unadjuvanted peptide was non-immunogenic or weakly immunogenic in all cases.

For both IgE and CD4 vaccines, the results of immunizations indicated that immunostimulatory complexes were adjuvanting and titers by week 9 were slightly less than or comparable to those obtained with w/o emulsions, irrespective of whether the emulsions were prepared by homogenized or extruded techniques as shown in FIGS. 7-10.

The combination systems with immunostimulatory complex dispersed as w/o emulsions prepared by either method consistently provided the highest sustained immune responses. As depicted in FIGS. 7-10, the antibody titers elicited from week 11 through week 17, for both IgE and CD4 immunogens were found to be on the order of a log unit or more higher than antibody titers obtained with either the immunostimulatory complex alone or the w/o emulsions with peptide alone. The sole exception to this being the CD4 w/o emulsions prepared by homogenization, where this separation is not found until week 17.

This observation is further supported by data obtained from the CD4 peptide competitive inhibition and virus neutralization studies highlighted in Tables 6 and 7, wherein the immune sera to the w/o emulsion combination systems with CD4 peptide/CpG oligonucleotides (charge ratio CD4:CpG2=2:1) competitively inhibited the highest level of B4 monoclonal antibody compared to the immune sera to the simple w/o emulsions or immunostimulatory complex with CD4 peptides alone. Moreover, the same formulations are shown to be the most effective at eliciting neutralizing activity against infectious virus.

Small differences are noted between the homogenized or extruded preparations and include the rate with which the titers elicited to IgE or CD4 immunogens obtained by ELISA were observed to peak. The immune responses peaked earlier (wk 9) for the extruded w/o emulsions, although the duration of the responses obtained are good (essentially equivalent by week 11 and slightly reduced by week 17). The analogous homogenized system peaked a little later (week 11) and provided sustained responses as can be seen by the high titers persisting at week 17.

This trend is also supported by data obtained from the CD4 peptide/mAbB4-HRP competitive inhibition assay and the virus neutralization studies highlighted in Tables 6 and 7.

By week 9, assays on sera obtained from animals immunized by the w/o emulsion system prepared from uncomplexed CD4 peptides via homogenization (87.2%) or by extrusion (88.6%) have been shown to competitively inhibit high levels of B4 monoclonal antibody. These were found to be the same order of magnitude (within experimental error) as for sera obtained from animals immunized with the w/o emulsion combination systems of CD4 peptide/CpG2 oligonucleotides (2:1) prepared via homogenization (70.1%) or by extrusion (94.9%). By week 17, assays on sera obtained from animals immunized by the w/o emulsion system prepared from uncomplexed CD4 peptides via homogenization (11.2%) or by extrusion (42.6%) competitively inhibited dramatically lower levels of B4 monoclonal antibody. The degree of inhibition were no longer generally comparable with that obtained for sera from animals immunized with the w/o emulsion combination systems of CD4 peptide/CpG2 oligonucleotides (2:1) prepared via homogenization (85.0%) or by extrusion (77.2%) processes.

Moreover, the same trend is shown for sera obtained from formulations of CD4 peptides when assayed for neutralization of infectious HIV-1 virus.

By week 9, assays on sera obtained from animals immunized by the w/o emulsion system prepared from uncomplexed CD4 peptides via homogenization (73% for 50% virus neutralization or 27% for 90% virus neutralization) or by extrusion (31% for 50% virus neutralization or 12% for 90% virus neutralization) neutralized essentially the same percentages of infectious HIV-1 virus (within experimental error). Assays on sera obtained from animals immunized with the w/o emulsion combination systems of CD4 peptide/CpG2 oligonucleotides (2:1) prepared via homogenization (12% for 50% virus neutralization or <10% for 90% virus neutralization) or by extrusion (103% for 50% virus neutralization or 33% for 90% virus neutralization) has shown that the homogenized system is significantly less effective at generating neutralizing antibodies against infectious HIV-1 virus at this time point. By week 11, assays on sera obtained from animals immunized by the w/o emulsion system prepared from uncomplexed CD4 peptides via homogenization (57% for 50% virus neutralization or 17% for 90% virus neutralization) or by extrusion (<10% for 50% virus neutralization or <10% for 90% virus neutralization) demonstrated that the capacity to neutralize infectious HIV-1 virus is reduced or eliminated (within experimental error). Assays on sera obtained from animals immunized with the w/o emulsion combination systems of CD4 peptide/CpG oligonucleotides (2:1) prepared via homogenization (40% for 50% virus neutralization or 30% for 90% virus neutralization) or by extrusion (120% for 50% virus neutralization or 39% for 90% virus neutralization) has clearly shown that both the homogenized and extruded systems were now effective at eliciting neutralizing antibody responses against infectious HIV. The response for the homogenized system was shown to be delayed relative to the extruded composition.

One possible explanation for these trends may be that w/o emulsions prepared via low energy extrusion processes can interact or present complexed immunogens more efficiently at earlier time points to immune effector cells, whereas the high energy homogenization process, provides a more uniform emulsion and essentially acts as a more efficient depot. The immune responses obtained by such a system would be anticipated to be delayed and potentially more sustainable.

The combination of the immunostimulatory complex and residual uncomplexed peptides dispersed in w/o emulsions were found to synergistically enhance the overall titers for both the IgE and CD4 immunogens. The method of preparation can influence the kinetics and duration of the responses, with both homogenization and extrusion shown to be compatible for preparing an efficacious vaccine.

In addition, in a separate study we examined the effect of CpG dose on immune responses. For both IgE and CD4 immunogens, immunostimulatory complexes were prepared from varying doses of CpG1 or CpG2 oligonucleotides (i.e. IgE:CpG1=4:1 or 1:1 and CD4:CpG2=2:1 or 1:2) and administered in either an aqueous buffer or dispersed in a w/o emulsion. All compositions were found to be immunogenic, however, in both studies the smaller relative dose of oligonucleotide (excess of synthetic peptide immunogen to oligonucleotide) elicited the superior immune responses in terms of absolute titer and of duration. In the case of IgE peptides/CpG1 oligonucleotides the ranking follows the order 4:1 charge ratio>1:1 neutral charge ratio whereas for CD4 peptides/CpG2 oligonucleotides the ranking follows the order 2:1 charge ratio>1:2 charge ratio. Most often improved adjuvanticity can be correlated with increasing doses of adjuvants. In these Examples, we have demonstrated the unexpected advantages of co-formulating stabilized immunostimulatory complex and uncomplexed peptide for maximum synergy of immune responses.

Thus, it can be concluded that immunostimulatory complex prepared from IgE or CD4 immunogens as described in this Example can effectively adjuvant immune responses in vivo. The responses obtained are comparable to those found for these same immunogens dispersed in w/o emulsions, however, it is anticipated that fewer reactogenicity issues would result from use of the fully aqueous dispersable immunostimulatory complex of synthetic immunogens as opposed to dispersing synthetic immunogens as w/o emulsions.

In this Example we have demonstrated that the delivery of IgE or CD4 immunogens as immunostimulatory complexes in combination with uncomplexed peptides dispersed within a water-in-oil emulsion vehicle provided the most effective presentation of immunogen to the immune system. The immune responses obtained for the combined system are significantly greater than the sum of the immune responses obtained for each system independently.

Furthermore, assays of sera obtained from animals immunized with combinations of immunostimulatory complex of CD4 immunogens and uncomplexed CD4 immunogens dispersed within a water-in-oil emulsion vehicle were shown to be more effective than simple w/o emulsions of uncomplexed CD4 immunogens at competitively inhibiting B4 monoclonal antibody. Moreover these same systems were shown to be the most effective at neutralizing infectious HIV-1 virus.

In the guinea pig model, the quantity and longevity of the immune responses obtained indicated that immunostimulatory complex derived from IgE/CpG1 and CD4/CpG2 combinations were preferred. It was experimentally determined that compositions derived from the alternative pairings of IgE/CpG2 and CD4/CpG1 were adjuvanting, although not to the same extent.

The possibility for fewer and lower (immunogen/adjuvant) dose regimens is indicated by these results. In cases where reactogenicity is a problem the combination system opens up the possibility of administering a smaller volume of emulsion with similar or higher levels of immunogenicity.

Specifically, this Example strongly indicates the potential of these new combination based formulations for development as efficacious dosage forms.

Example 8

The Immunogenicity of IgE and CD4 Peptide Immunogens Formulated as Immunostimulatory Complex or as In-Situ Gelling Polymer Solutions or in Combinations This Example illustrates the immunogenicity of IgE and CD4 peptide immunogens formulated as immunostimulatory complex with CpG1 or CpG2 oligonucleotides or as in-situ gelling polymers and biocompatible solvents or as immunostimulatory complex suspended in in-situ gelling polymers and biocompatible solvents in guinea pigs, which were immunized intramuscularly. Lyophilized peptide immunogens or immunostimulatory complex derived from peptide immunogens and CpG oligonucleotides were prepared as described in Examples 3. The in-situ gelling polymers were prepared as described in Example 6a/6b.

To examine the immunogenicity of IgE and CD4 peptide immunogens formulated as in-situ gelling polymers (Resomer® RG 504H) or as immunostimulatory complexes with CpG1 or CpG2 oligonucleotides suspended in in-situ gelling polymers (Resomer® RG 504H) formed in accordance with the present invention, groups of three, 6 to 8 week old female guinea pigs (Covance Research Products Inc, Denver, Pa.) were immunized intramuscularly (I.M.) with the following amounts of immunogen on week 0: 300 μg of lyophilized IgE peptides/CpG1 immunostimulatory complex (4:1 charge ratio) reconstituted and suspended in a final volume of 200 μL PBS (pH 7.4), prepared as described in Table 4, or 300 μg of CD4 peptides/CpG2 immunostimulatory complex (2:1 charge ratio) reconstituted and suspended in a final volume of 200 μL PBS (pH 7.4), prepared as described in Table 4, or 300 μg of IgE peptides reconstituted and suspended in 200 μL of Resomer® RG 504H (20% by wt) dissolved in dimethyl sulfoxide (DMSO) or 300 μg of CD4 peptides reconstituted and suspended in 200 μL of Resomer® RG 504H (20% by wt) dissolved in dimethyl sulfoxide (DMSO) or 300 μg of lyophilized IgE peptides/CpG1 immunostimulatory complex (4:1 charge ratio), prepared as described in Table 4, reconstituted and suspended in 200 μL of Resomer® RG 504H (20% by wt) dissolved in dimethyl sulfoxide (DMSO) or 300 μg of lyophilized CD4 peptides/CpG2 immunostimulatory complex (2:1 charge ratio), prepared as described in Table 4, reconstituted and suspended in 200 μL of Resomer® RG 504H (20% by wt) dissolved in dimethyl sulfoxide (DMSO).

The guinea pigs showed no gross pathologies or behavioral changes after receiving immunostimulatory complex, in-situ gelling polymers in DMSO containing peptide immunogens or in-situ gelling polymers in DMSO containing immunostimulatory complex. Sera were obtained on weeks +3, +6, +9, +12 and were evaluated for the presence of anti-IgE antibodies in the case of IgE immunogens or anti-CD4 antibodies in the case of CD4 immunogens, by immunogen-specific ELISAs following the procedures described in Example 7.

Immunogenicity Results

Figure 11:
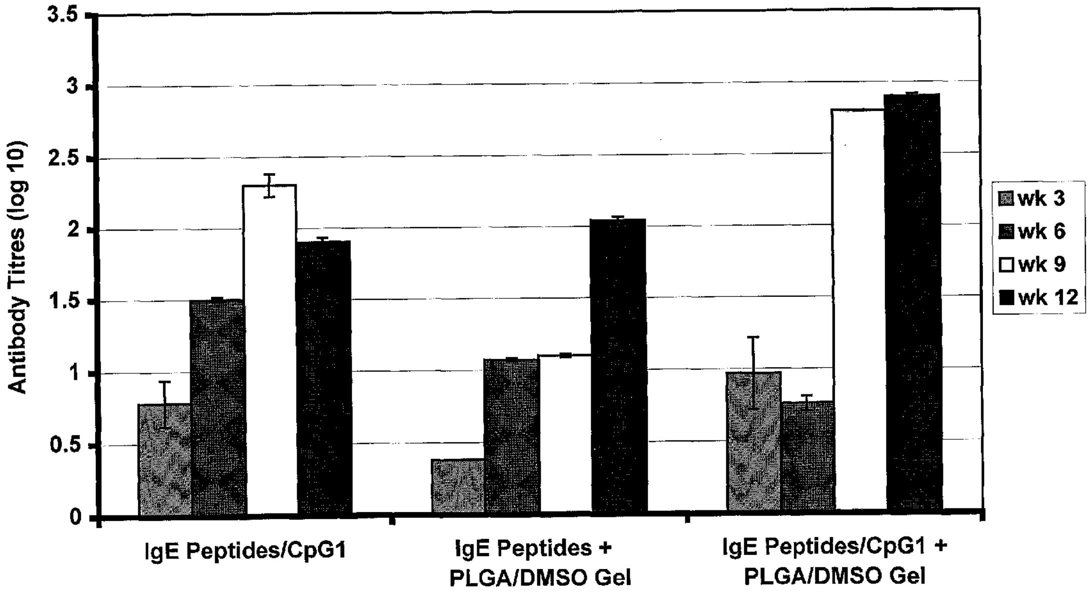
FIG. 11 shows the serum IgG responses in guinea pigs immunized intramuscularly (I.M.) in accordance with the following immunization protocols. Groups of 3 guinea pigs were immunized on week 0 with three different preparations: 300 μg of an immunostimulatory complex of IgE peptides and CpG1 reconstituted in 200 μL of PBS, pH 7.4; 300 μg of IgE peptides reconstituted in a biocompatible DMSO solution of an in-situ gelling biodegradable PLGA copolymer in 200 μL dose volume of DMSO; or 300 μg of an immunostimulatory complex of IgE peptides and CpG1 reconstituted in a biocompatible solution of DMSO and an in-situ gelling biodegradable PLGA copolymer in 200 μL dose volume of DMSO. Sera obtained on weeks +3, +6, +9, and +12 were evaluated for the presence of anti-IgE peptide antibodies using an enzyme-linked immunosorbent assay (ELISA).
Figure 12:
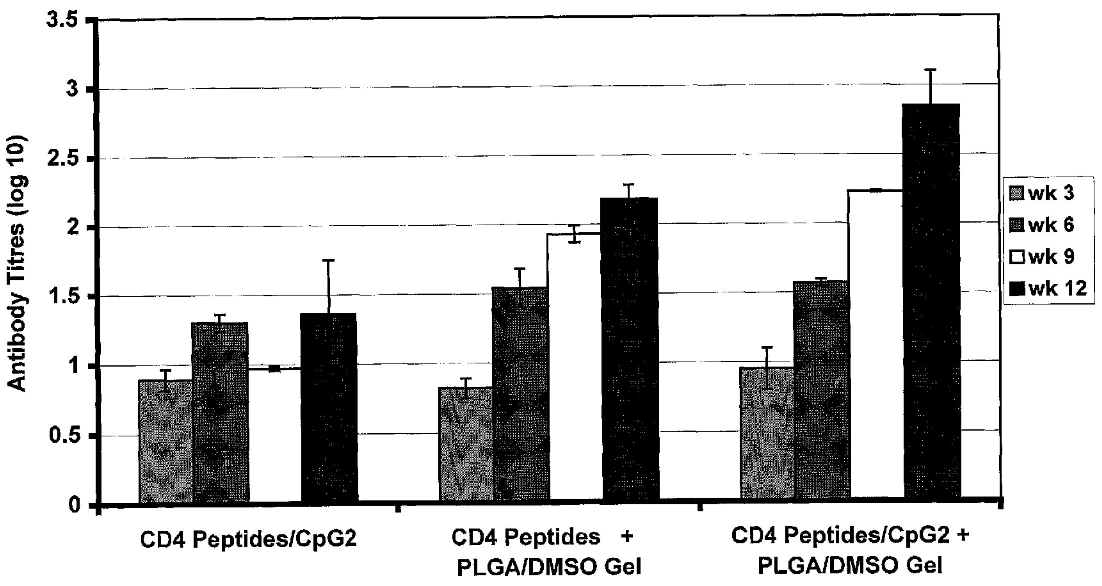
FIG. 12 shows the serum IgG responses in guinea pigs immunized intramuscularly (I.M.) following various immunization protocols by a cocktail of CD4 peptide immunogens. Groups of 3 guinea pigs were immunized on week 0 with 300 μg of an immunostimulatory complex derived from a cocktail of CD4 peptides and CpG2 constructs reconstituted in 200 μL of PBS, pH 7.4 or 300 μg of CD4 peptides reconstituted from a biocompatible solution of DMSO which additionally contains an in-situ gelling biodegradable PLGA copolymer (200 μL dose volume) or 300 μg of an immunostimulatory complex derived from a cocktail of CD4 peptides and CpG2 constructs reconstituted from a biocompatible solution of DMSO which additionally contains an in-situ gelling biodegradable PLGA copolymer (200 μL dose volume). Sera obtained on weeks +3, +6, +9 and +12 were evaluated for the presence of anti-CD4 peptide antibodies using an enzyme-linked immunosorbent assay (ELISA).

The serum antibody titers following single-dose immunization of IgE immunogens are shown in FIG. 11 and for CD4 immunogens are shown in FIG. 12. Control experiments demonstrated that unadjuvanted peptide was non-immunogenic or weakly immunogenic in either case. In both studies, the results of immunizations indicated that immunostimulatory complex alone were moderately adjuvanting with the titers peaking by week 9. Conversely, uncomplexed immunogens suspended in in-situ gelling polymers-were also weakly adjuvanted with peak responses observed at week 12.

For both IgE and CD4 immunogens, the derived immunostimulatory complexes suspended as an in-situ gelling polymer elicited the highest immune responses. These responses were seen to peak around week 9 and were sustainable through week 12. The quantity and duration of the immune responses obtained were not found with either the immunostimulatory complex alone or with uncomplexed immunogens administered in a composition including in-situ gelling polymer alone.

It is expected that small molecular weight immunogens such as peptides can easily diffuse through polymer implants and gels resulting in large quantities of burst release upon injection. The physical factors that control gellation can be adjusted to retard this process; however, the mass of peptide so released is essentially unadjuvanted and subject to the standard degradation processes that are normally experienced in vivo. In addition, the small amounts of material remaining encapsulated may not be expected to be sufficient for an efficient boost once the polymer degrades, necessitating much larger doses of peptide. The residual DMSO trapped within the matrix also presents stability issues, wherein sensitive amino acids contained in the peptides could be oxidized. Furthermore it has been well established that water can penetrate these materials at varying rates depending on various factors such as gel micromorphology, polymer hydrophobicity and crystallinity.[45, 46] Water penetrating the matrix will promote bulk hydrolysis, the prime degradation mechanism operating on PLG/PLGA copolymers in vivo This process is known to be accompanied by dramatic local pH changes, which can essentially reduce the pH to 2 or 3.[67] The free uncomplexed solubilized peptides may not be stable to such an environment, and this further limits the potential for these systems. Acid buffering agents may be employed to help to offset these problems, but cannot be considered ideal. Encapsulating a suspension of peptide immunogens in the form of an immunostimulatory complex imparts a number of stability and adjuvantation advantages for this system. Once the injection of polymer gel is made, the small amounts of complex not effectively encapsulated in the gel (presumably surface located near the gelling front) can serve to initiate or prime the immune response more effectively than uncomplexed peptide immunogen alone. The CpG oligonucleotide remains in close contact with peptide immunogen and in the form of a complex particulate may further protect and stabilize the peptide immunogen from enzymatic digestion in vivo or from chemical instabilities which may be due to the DMSO solvent contained within the matrix.

Furthermore, the peptide immunogens remaining entrapped in the matrix in a particulate form would be expected to be better protected against the acidification process than free uncomplexed peptides. Immunogens presented in this form can be expected to provide a more efficient boost of immunogen to the immune system eliciting stronger and longer lasting immune responses than otherwise possible in a single-dose controlled release formulation.

In control experiments, it was determined that solutions of uncomplexed peptide immunogens dissolved in polymer compositions of RG 504H (20% by wt) in DMSO gelled rapidly when placed in contact with solutions of PBS. Separating the solution from gel phase for these samples and analyzing the solutions by ultraviolet spectroscopy at λ=280 nm. revealed that sizeable amounts of uncomplexed peptide (c.a. 50-70%) were co-extracted with the DMSO.

The combination of the immunostimulatory complex and uncomplexed peptide immunogens suspended in in-situ gelling polymers have been found to synergistically enhance the overall titers for both the IgE and CD4 immunogens in these controlled release preparations.

A separate study examining the effect of CpG oligonucleotide dose on immune responses was not conducted in this study. It would be expected that further improvement in the absolute titers, may be obtained by employing immunostimulatory complex prepared near electrical neutrality or with an excess of negative charge supplied by either CpG oligonucleotide or alternatively an additional compatible excipient. In these compositions the majority of the peptide immunogen is bound as an immunostimulatory complex and the gellation process upon injection does not result in major loses of unadjuvanted peptide by virtue of co-extraction in the biocompatible solvent.

Thus, it can be concluded that immunostimulatory complex can both stabilize peptide immunogens as immunostimulatory complex and that these compositions when combined with an in-situ gelling polymer can effectively adjuvant the immune responses in vivo. This is particularly important for these polymer systems which are intended for single-dose use. The delivery of immunogens as immunostimulatory complex suspended within an in-situ gelling polymer vehicle provides the most efficient presentation of immunogen to the immune system. The responses obtained for the combined system are significantly greater than the sum of the immune responses obtained for each system independently and are sustainable, unlike in-situ gels prepared by simple reconstitution of uncomplexed peptide immunogens from polymers in biocompatible solvents.

In the guinea pig model, the quantity and longevity of the responses obtained indicated that immunostimulatory complexes derived from IgE/CpG1 and CD4/CpG2 combinations were preferred. It was experimentally determined that compositions derived from the alternative pairings of IgE/CpG2 and CD4/CpG1 were adjuvanting, although not to the same extent.

The possibility of a single-dose regimen is indicated by these results. Specifically, this Example strongly indicates the potential of these new instantly reconstituted combination-based formulations for development as efficacious controlled release dosage form.

TABLE 1

Synthetic Peptide Immunogens And Oligonucleotides Physical Properties

| Vaccine | SEQ ID No: | Sequence | IP | FW |
|---|---|---|---|---|
| HIV (CD4) | 4 | ISITEIKGVIVHRIETILF-(εK) CNQGSFLTKGPSKLNDRADS-RRSLWDQGNC | 9.30 | 5646 |
| Vaccine | 5 | KKKTDRVIEVLQRAGRAIL-(εK) CNQGSFLTKGPSKLNDRADS-RRSLWDQGNC | 10.30 | 5659 |
| | 6 | ISITEIKGVIVHRIETILF-(εK) CHASIYDFGSC | 6.91 | 3493 |
| Prostate Cancer | 7 | KKQYIKANSKFIGITELEHWSYGLRPG | 9.70 | 3164 |
| (LHRH) Vaccine | 8 | TAKSKKFPSYTATYQFGGFFLLTRILTIPQSLEGGEHWSYGLRPG | 9.70 | 5052 |
| | 9 | TAKSKKFPSYTATYQFGGLSEIKGVIVHRLEGVGGEHWSYGLRPG | 9.60 | 4910 |
| Allergy (IgE) | 10 | KKKIITITRIITIITTID-(εK) CGETYQSRVTHPHLPRALMR STTKC | 10.31 | 5068 |
| Vaccine | 11 | ISITEIKGVIVHRIETILF-(εK) CGETYQSRVTHPHLPRALMR STTKC | 9.69 | 5165 |

| Oligonucleotide | Sequence | Tm | FW |
|---|---|---|---|
| SEQ ID No: 1 | 5' - TCG TCG TTT TGT CGT TTT GTC GTT TTG TCG TT - 3' | 77.1° C. | 9900 |
| SEQ ID No: 2 | 5' - nTC GTC GTT TTG TCG TTT TGT CGT T - 3'<br>n = phosphorothioate group | 70.9° C. | 7400 |

IP = Theoretical Ionization Potential, (ref. 68)
FW = Formula Weight
Tm = Primer to target Tm (by % GC)

TABLE 2

Molar Charge Calculations
Synthetic Peptide Immunogens And Oligonucleotides

| Vaccine | SEQ ID No: | Net Calculated Charge | % Molar Peptide Contribution In Vaccine | Avg. Total Molar Equivalents +'ve Charge | FW | Avg. Total Peptide FW |
|---|---|---|---|---|---|---|
| CD4 | 4 | 4 +'ve | 50% | 1 nmol = 4.3 nmol | 5646 | 5280.6 |
| Vaccine | 5 | 7 +'ve | 25% | +'ve charge | 5659 | |
| | 6 | 2 +'ve | 25% | | 3493 | |
| IgE | 10 | 7 +'ve | 66.6% | 1 nmol = 7.7 nmol | 5068 | 5132.1 |
| Vaccine | 11 | 9 +'ve | 33.3% | +'ve charge | 5165 | |
| LHRH | 7 | 4 +'ve | 33.3% | 1 nmol = 4.3 nmol | 3164 | 4543.9 |
| Vaccine | 8 | 5 +'ve | 33.3% | +'ve charge | 5052 | |
| | 9 | 4 +'ve | 33.3% | | 4910 | |

Net charge: Calculated by assigning a +1 charge for each lysine (K), arginine (R) or histidine (H), a −1 charge for each aspartic acid (D) or glutamic acid (E) and a charge of 0 for every other amino acid within the sequence. The charges are summed for each peptide and expressed as the net average charge.
Average Total Molar Equivalents Of +'ve Charge From Peptides: Estimates for the average charge of the combined peptide mixture are calculated by summing the overall molar charge contribution for each component within the mixture.
Average Total Peptide Formula Weight (FW): Estimates for the average Total peptide FW are calculated by summing the overall molar mass contribution for each component within the mixture.
Molar Equivalents Of −'ve charge From CpG Oligonucleotides: Each phosphorothioate group contributes −1 charge.
CpG1 (32 base oligomer) − 1 nmol CpG1 = 32.0 nmol −'ve charge
CpG2 (24 base oligomer + phosphorothioate). −1 nmol CpG2 = 25.0 nmol −'ve charge

TABLE 3

| Calculated Molar Charge Ratios Used To Prepare Complexes LHRH Peptide Immunogens And CpG1 Oligonucleotides | | | |
|---|---|---|---|
| Final Charge Ratio (LHRH:CpG1) | nmols of LHRH by Charge for the Final Charge Ratio of LHRH:CpG1 (LHRH of Fixed Mass)[1,2] (nmols +'ve charge) | Total nmol of CpG1 used[3] | Calculated Mass CpG1 Required FW = 9,900 μg/μmol (Table 2) (stock A = 2.0 μg/μL) |
| 8:1 | 94.6/8 = 11.8 (~8:1 ratio) | 11.8/32 = 0.37 | 3.6 μg = 1.9 μL stock A |
| 4:1 | 94.6/4 = 23.7 (~4:1 ratio) | 23.7/32 = 0.74 | 7.3 μg = 3.7 μL stock A |
| 2:1 | 94.6/2 = 47.3 (~2:1 ratio) | 47.3/32 = 1.48 | 14.7 μg = 7.4 μL stock A |
| 1:1 | 94.6/1 = 94.6 (~1:1 ratio) | 94.6/32 = 2.96 | 29.3 μg = 14.7 μL stock A |
| 1:2 | 94.6/0.5 = 189.2 (~1:2 ratio) | 189.2/32 = 5.92 | 58.6 μg = 29.3 μL stock A |

[1]Total calculated + 've molar charge for 100 μg of LHRH peptides:
FW = 4543.9 μg/umol (Table 2).
Total + 've molar charge LHRH peptides = 4.3 nmol +'ve charge/nmol LHRH peptide (Table 2)
In 100 μg LHRH peptides there are 100 μg /4543.9 μg/umol = 22.0 nmol of LHRH immunogen
Total + 've molar charge = 22.0 nmol × 4.3 nmols +'ve charge/nmol LHRH peptides = 94.6 nmols +'ve charge
[2]Sample calculation:
Final 8:1 molar charge ratio of LHRH immunogen to CpG1 oligonucleotide.
100 μg of LHRH contributes 94.6 nmols of +'ve charge.
To establish an 8:1 molar charge ratio of LHRH to CpG1 in solution the required amount of LHRH that must be neutralized by CpG1 is calculated as 94.6 nmols +'ve charge/8 = 11.8 nmols +'ve charge.
Thus 11.8 nmols +'ve charge contributed by LHRH must be neutralized by 11.8 nmols of –'ve charge contributed by CpG1.
[3]# nmol of –'ve molar charge contributed by CpG1:
Total calculated –'ve molar charge for CpG1 Oligonucleotides
1 nmol of CpG1 = 32 nmol –'ve charge (Table 2)

TABLE 4

| Molar Charge Ratio Calculations IgE And CD4 Peptide Immunogens And CpG Oligonucleotides | | | | |
|---|---|---|---|---|
| Formulation | Dose peptide | Calculated Charge Ratios nmols IgE: nmols CpG1 (+/–)[1] nmols CD4: nmols CpG2 (+/–)[2] | nmol of CpG1 or CpG2 used[3] | Calculated Mass/Volume of CpG1 or CpG2 required (CpG1 – Stock A = 2.0 μg/μL) (CpG2 – Stock B = 2.0 μg/μL) |
| IgE – | 100 μg | 150:163.2~1:1, neutral charge ratio | 5.1 nmol CpG1 | 50 μg CpG1 = 25 μL stock A |
| w/o emulsions | 100 μg | 150:35.2~4:1, +'ve charge ratio | 1.1 nmol CpG1 | 11.1 μg CpG1 = 5.6 μL stock A |
| IgE – | 300 μg | 451:489.6~1:1, neutral charge ratio | 15.2 nmol CpG1 | 150 μg CpG1 = 75 μL stock A |
| polymer gels | 300 μg | 451:107.7~4:1 +'ve charge ratio | 3.4 nmol CpG1 | 33.3 μg CpG1 = 16.8 μL stock A |
| CD4 – | 100 μg | 81.3:170~1:2, –'ve charge ratio | 6.8 nmol CpG2 | 50 μg CpG2 = 25 μL stock B |
| w/o emulsions | 100 μg | 81.3:37.5~2:1, +'ve charge ratio | 1.5 nmol CpG2 | 11.1 μg CpG2 = 5.6 μL stock B |
| CD4 – | 300 μg | 244.2:507.5~1:2, –'ve charge ratio | 20.3 nmol CpG2 | 150 μg CpG2 = 75 μL stock B |
| polymer gels | 300 μg | 244.2:112.5~2:1, +'ve charge ratio | 4.5 nmol CpG2 | 33.3 μg CpG2 = 16.8 μL stock B |

[1]Total calculated +'ve molar charge for 100 μg or 300 μg of IgE peptides:
FW = 5132.1 μg/μmol (Table 2); Total +'ve molar charge IgE peptides = 7.7 nmol +'ve charge/nmol IgE peptides (Table 2)
In 100 μg IgE peptides there are 100 μg/5132.1 μg/μmol = 19.5 nmol of IgE immunogen
Total +'ve molar charge = 19.5 nmol × 7.7 nmols +'ve charge/nmol IgE peptides = 150.1 nmols +'ve charge
In 300 μg IgE peptides there are 300 μg/5132.1 μg/μmol = 58.5 nmol of IgE immunogen
Total +'ve molar charge = 58.5 nmol × 7.7 nmols +'ve charge/nmol IgE peptides = 450.5 nmols +'ve charge
[2]Total calculated +'ve molar charge for 100 μg or 300 μg of CD4 peptides:
FW = 5280.6 μg/□mol (Table 2); Total +'ve molar charge CD4 peptides = 4.3 nmol +'ve charge/nmol CD4 peptides (Table 2)
In 100 μg CD4 peptides there are 100 μg/5280.6 μg/μmol = 18.9 nmol of CD4 immunogen
Total +'ve molar charge = 18.9 nmol × 4.3 nmols +'ve charge/nmol CD4 peptides = 81.3 nmols +'ve charge
In 300 μg CD4 peptides there are 300 μg/5280.6 μg/μmol = 56.8 nmol of CD4 immunogen
Total +'ve molar charge = 56.8 nmol × 4.3 nmols +'ve charge/nmol CD4 peptides = 244.2 nmols +'ve charge
[3]# nmol of –'ve charge contributed by CpG1 or CpG2:
Total calculated –'ve molar charge for CpG1/CpG2 oligonucleotides
1 nmol of CpG1 = 32 nmol –'ve charge, FW = 9,900 μg/μmol (Table 2)
1 nmol of CpG2 = 25 nmol –'ve charge, FW = 7,400 μg/μmol (Table 2)

TABLE 5

| Comparison Of Physical Properties Of PLG/PLGA Copolymers Dissolved In DMSO As A Function Of Weight Percent In Solution | | | |
|---|---|---|---|
| Polymer Identity (ratio D,L-lactide:glycolide) | Polymer Properties Molecular Weight (g/mol) Inherent Viscosity (dl/g) | Wt % Polymer in DMSO (Wt/Wt %) | Viscosity (mPa) |
| RG 502H (50:50) | Mw = 8,033, I.V. = 0.2 | 44.0% | 86.7 |
| RG 503H (50:50) | Mw = 25,760, I.V. = 0.3 | 30.0% | 226.2 |
| RG 503H (50:50) | Mw = 25,760, I.V. = 0.3 | 24.0% | 99.6 |
| RG 503H (50:50) | Mw = 25,760, I.V. = 0.3 | 20.0% | 55.1 |

TABLE 5-continued

Comparison Of Physical Properties Of PLG/PLGA Copolymers Dissolved In DMSO As A Function Of Weight Percent In Solution

| | | | |
|---|---|---|---|
| RG 503H (50:50) | Mw = 25,760, I.V. = 0.3 | 17.3% | 34.0 |
| RG 504H (50:50) | Mw = 43,110, I.V. = 0.4 | 30.4% | 418.4 |
| RG 504H (50:50) | Mw = 43,110, I.V. = 0.4 | 24.5% | 187.5 |
| RG 504H (50:50) | Mw = 43,110, I.V. = 0.4 | 20.5% | 104.3 |
| RG 504H (50:50) | Mw = 43,110, I.V. = 0.4 | 17.6% | 63.3 |
| RG 504H (50:50) | Mw = 43,110, I.V. = 0.4 | 15.4% | 44.5 |
| RG 756 (75:25) | Mw = 81,970, I.V. = 0.8 | 33.0% | — |
| RG 756 (75:25) | Mw = 81,970, I.V. = 0.8 | 24.5% | — |
| RG 756 (75:25) | Mw = 81,970, I.V. = 0.8 | 19.4% | 252.0 |
| RG 756 (75:25) | Mw = 81,970, I.V. 0.8 | 16.0% | 138.3 |
| RG 756 (75:25) | Mw = 81,970, I.V. = 0.8 | 13.6% | 102.2 |
| RG 756 (75:25) | Mw = 81,970, I.V. = 0.8 | 11.9% | 68.0 |

| Polymer | Percentage by weight required for a solution with apparent viscosity of ~100 mPa |
|---|---|
| RG-503H | ~24% |
| RG-504H | ~20.5% |
| RG-756 | ~13.6% |

TABLE 6

B4-HRP Inhibition Assay Of Sera Obtained From CD4 Peptides, CD4/CpG2 Immunostimulatory Complexes Or Combinations In W/O Emulsions

| Formulation | % Inhibition* (week 9) | % Inhibition* (week 11) | % Inhibition* (week 17) |
|---|---|---|---|
| CD4 peptide unadjuvanted | 5% | 49.1%** | 8.2% |
| CD4/CpG2 (2:1) | 12.8% | 2.7% | N.D. |
| CD4/(w/o) emulsion*** | 87.2% | 87.5% | 11.2% |
| CD4/CpG2 (2:1)/(w/o) emulsion*** | 70.1% | 92.1% | 85.0% |
| CD4/(w/o) emulsion**** | 88.6% | 61.4% | 42.6% |
| CD4/CpG2 (2:1)/(w/o) emulsion**** | 94.9% | 95.3% | 77.2% |
| Positive Controls | | | |
| mAb B4, 20 μg/mL | 63% | 63% | 48.7% |
| mAb B4, 2.0 μg/mL | 23.5% | 11.7% | 11.7% |

*N.D. samples were not assayed

**The value of 49.1% at week 11 for unadjuvanted CD4 peptide is unexpected and likely due to experimental error.

***Water-in-oil emulsion prepared with ISA 720 via homogenization techniques

****Water-in-oil emulsion prepared with ISA 720 via extrusion techniques

TABLE 7

Neutralization Of HIV-1 Strain VL135 By Immune Sera To CD4 Peptides CD4/CpG2 Immunostimulatory Complexes Or Combinations In W/O Emulsions (MT-2 microplaque assay)

| Formulation | HIV-1 Strain VL135 50% Inhibition* (week 9) | HIV-1 Strain VL135 50% Inhibition* (week 11) | HIV-1 Strain VL135 90% Inhibition* (week 9) | HIV-1 Strain VL135 90% Inhibition* (week 11) |
|---|---|---|---|---|
| CD4 peptide unadjuvanted | <10% | <10% | <10% | <10% |
| CD4/(w/o) emulsion** | 73% | 27% | 57% | 17% |
| CD4/CpG2 (2:1 charge ratio)/ (w/o) emulsion** | 12% | 40% | <10% | 30% |
| CD4/(w/o) emulsion*** | 31% | <10% | <10% | <10% |
| CD4/CpG2 (2:1 charge ratio)/ (w/o) emulsion*** | 103% | 120% | 33% | 39% |
| Positive Controls | | | | |
| mAb B4 | 0.078 μg/mL | 0.13 μg/mL | 0.27 μg/mL | 0.32 μg/mL |
| mAb B4 | 0.18 μg/mL | 0.13 μg/mL | 0.32 μg/mL | 0.31 μg/mL |

*Reciprocal titer prior to the addition of an equal volume of virus containing 1-1.3 logs

**Water-in-oil emulsion prepared with ISA 720 by homogenization techniques

***Water-in-oil emulsion prepared with ISA 720 by extrusion techniques

What I claim is:

1. A stabilized immunostimulatory microparticulate complex comprising a cationic peptide immunogen wherein the peptide immunogen comprises a target B cell antigen or a CTL epitope and a T helper cell epitope and an anionic CpG oligonucleotide wherein the cationic peptide immunogen has a net positive charge at a pH in the range of 5.0 to 8.0 calculated by assigning a +1 charge for each lysine (K), arginine (R) or histidine (H), a −1 charge for each aspartic acid (D) or glutamic acid (E) and a charge of 0 for all other amino acids in the peptide immunogen and wherein the anionic CpG oligonucleotide has a net negative charge at a pH in the range of 5.0-8.0 and is a single-stranded DNA comprising 8 to 64 nucleotide bases with a repeat of a cytosine-guanidine motif and the number of repeats of the CpG motif is in the range of 1 to 10, and wherein the cationic peptide immunogen:CpG oligonucleotide charge ratio ranges from 8:1 to 1:2 and wherein the microparticulate complex is a precipitate with an average particle size of about 22.5 microns or less.

2. The immunostimulatory microparticulate complex of claim 1, wherein the cationic peptide immunogen is a mixture of synthetic peptide immunogens.

3. The immunostimulatory microparticulate complex of claim 1, wherein the net positive charge of the cationic peptide immunogen is at least +2.

4. The immunostimulatory microparticulate complex of claim 2, wherein the average net positive charge of the mixture of synthetic peptide immunogens is at least +2.

5. The immunostimulatory microparticulate complex of claim 4, wherein the net negative charge of the anionic oligonucleotide is at least −2.

6. The immunostimulatory microparticulate complex of claim 1, wherein the CpG oligonucleotide is a single-stranded DNA molecules with 18-48 nucleotide bases and the number of repeats of CpG motif therein in the range of 3 to 8.

7. The immunostimulatory microparticulate complex of claim 1, wherein the CpG oligonucleotide has the formula: 5' $X^1CGX^2$3' wherein C and G are unmethylated; and $X^1$ is selected from the group consisting of A (adenine), G (guanine) and T (thymine); and $X^2$ is C (cytosine) or T (thymine).

8. The immunostimulatory microparticulate complex of claim 1, wherein CpG oligonucleotide is selected from a group consisting of 5' TCG TCG TTT TGT CGT TTT GTC GTT TTG TCG TT 3' (CpG1) SEQ ID NO: 1, a 32 base length oligomer, and 5'nTC GTC GTT TTG TCG TTT TGT CGT T 3' (CpG2) SEQ ID NO: 2, a 24 base length oligomer plus an phosphorothioate group designated as n.

9. The immunostimulatory microparticulate complex of claim 8, wherein CpG oligonucleotide is 5' TCG TCG TTT TGT CGT TTT GTC GTT TTG TCG TT 3' (CpG1) SEQ ID NO: 1.

10. The immunostimulatory microparticulate complex of claim 8, wherein the cationic peptide immunogen is a synthetic peptide conjugated to a T helper cell epitope.

11. The immunostimulatory microparticulate complex of claim 10, wherein the cationic immunogen is selected from the group consisting of SEQ ID NO: 7, 8 and 9 and a mixture thereof.

12. The immunostimulatory microparticulate complex of claim 1, wherein the cationic peptide immunogen:CpG oligonucleotide charge ratio ranges from 4:1 to 1:1.

13. The immunostimulatory microparticulate complex of claim 1, wherein the microparticulate complex is a precipitate with an average particle size of about 10 microns or less.

14. A stabilized immunostimulatory microparticulate complex comprising a cationic peptide immunogen wherein the peptide immunogen comprises a target B cell antigen or a CTL epitope and a T helper cell epitope and an anionic CpG oligonucleotide wherein the cationic peptide immunogen has a net positive charge at a pH in the range of 5.0 to 8.0 calculated by assigning a +1 charge for each lysine (K), arginine (R) or histidine (H), a −1 charge for each aspartic acid (D) or glutamic acid (E) and a charge of 0 for all other amino acids in the peptide immunogen and wherein the anionic CpG oligonucleotide has a net negative charge at a pH in the range of 5.0-8.0 and is a single-stranded DNA comprising 8 to 64 nucleotide bases with a repeat of a cytosine-guanidine motif and the number of repeats of the CpG motif is in the range of 1 to 10, and wherein the cationic peptide immunogen:CpG oligonucleotide charge ratio ranges from 8:1 to 1:2 and wherein the microparticulate complex is formed by combining the CpG oligonucleotide to the cationic peptide immunogen, or vice versa, in a dropwise manner to form a precipitate with an average particle size of about 22.5 microns or less.

15. The immunostimulatory microparticulate complex of claim 14, wherein the cationic peptide immunogen is a mixture of synthetic peptide immunogens.

16. The immunostimulatory microparticulate complex of claim 14, wherein the net positive charge of the cationic peptide immunogen is at least +2.

17. The immunostimulatory microparticulate complex of claim 15, wherein the average net positive charge of the mixture of synthetic peptide immunogens is at least +2.

18. The immunostimulatory microparticulate complex of claim 16 or 17, wherein the net negative charge of the anionic oligonucleotide is at least −2.

19. The immunostimulatory microparticulate complex of claim 14, wherein the CpG oligonucleotide is a single-stranded DNA molecules with 18-48 nucleotide bases and the number of repeats of CpG motif therein in the range of 3 to 8.

20. The immunostimulatory microparticulate complex of claim 14, wherein the CpG oligonucleotide has the formula: 5' X1CGX2 3' wherein C and G are unmethylated; and X1 is selected from the group consisting of A (adenine), G (guanine) and T (thymine); and X2 is C (cytosine) or T (thymine).

21. The immunostimulatory microparticulate complex of claim 14, wherein CpG oligonucleotide is selected from a group consisting of 5' TCG TCG TTT TGT CGT TTT GTC GTT TTG TCG TT 3' (CpG1) SEQ ID NO: 1, a 32 base length oligomer, and 5'nTC GTC GTT TTG TCG TTT TGT CGT T 3' (CpG2) SEQ ID NO: 2, a 24 base length oligomer plus an phosphorothioate group designated as n.

22. The immunostimulatory microparticulate complex of claim 21, wherein CpG oligonucleotide is 5' TCG TCG TTT TGT CGT TTT GTC GTT TTG TCG TT 3' (CpG1) SEQ ID NO: 1.

23. The immunostimulatory microparticulate complex of claim 21, wherein the cationic peptide immunogen is a synthetic peptide conjugated to a T helper cell epitope.

24. The immunostimulatory microparticulate complex of claim 23, wherein the cationic immunogen is selected from the group consisting of SEQ ID NO: 7, 8 and 9 and a mixture thereof.

25. The immunostimulatory microparticulate complex of claim 14, wherein the cationic peptide immunogen:CpG oligonucleotide charge ratio ranges from 4:1 to 1:1.

26. The immunostimulatory microparticulate complex of claim 14, wherein the microparticulate complex is a precipitate with an average particle size of about 10 microns or less.

* * * * *

SEQUENCE LISTING

```
<160> NUMBER OF SEQ ID NOS: 11

<210> SEQ ID NO 1
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 1

tcgtcgtttt gtcgttttgt cgttttgtcg tt                                32


<210> SEQ ID NO 2
<211> LENGTH: 24
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: n indicates phosphorothioate group

<400> SEQUENCE: 2

tcgtcgtttt gtcgttttgt cgtt                                         24


<210> SEQ ID NO 3
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 3

tcgtcgtttt gtcgttttgt cgtt                                         24


<210> SEQ ID NO 4
<211> LENGTH: 50
<212> TYPE: PRT
<213> ORGANISM: Human
<220> FEATURE:
<221> NAME/KEY: misc_feature
<222> LOCATION: (20)..(20)
<223> OTHER INFORMATION: Xaa indicates epsilon-Lys

<400> SEQUENCE: 4

Ile Ser Ile Thr Glu Ile Lys Gly Val Ile Val His Arg Ile Glu Thr
1               5                   10                  15

Ile Leu Phe Xaa Cys Asn Gln Gly Ser Phe Leu Thr Lys Gly Pro Ser
            20                  25                  30

Lys Leu Asn Asp Arg Ala Asp Ser Arg Arg Ser Leu Trp Asp Gln Gly
        35                  40                  45

Asn Cys
    50


<210> SEQ ID NO 5
<211> LENGTH: 50
<212> TYPE: PRT
<213> ORGANISM: Human
<220> FEATURE:
<221> NAME/KEY: misc_feature
<222> LOCATION: (20)..(20)
<223> OTHER INFORMATION: Xaa indicates epsilon-Lys

<400> SEQUENCE: 5
```

-continued

```
Lys Lys Lys Thr Asp Arg Val Ile Glu Val Leu Gln Arg Ala Gly Arg
1               5                   10                  15

Ala Ile Leu Xaa Cys Asn Gln Gly Ser Phe Leu Thr Lys Gly Pro Ser
            20                  25                  30

Lys Leu Asn Asp Arg Ala Asp Ser Arg Arg Ser Leu Trp Asp Gln Gly
        35                  40                  45

Asn Cys
    50


<210> SEQ ID NO 6
<211> LENGTH: 31
<212> TYPE: PRT
<213> ORGANISM: Human
<220> FEATURE:
<221> NAME/KEY: misc_feature
<222> LOCATION: (20)..(20)
<223> OTHER INFORMATION: Xaa indicates epsilon-Lys

<400> SEQUENCE: 6

Ile Ser Ile Thr Glu Ile Lys Gly Val Ile Val His Arg Ile Glu Thr
1               5                   10                  15

Ile Leu Phe Xaa Cys His Ala Ser Ile Tyr Asp Phe Gly Ser Cys
            20                  25                  30


<210> SEQ ID NO 7
<211> LENGTH: 27
<212> TYPE: PRT
<213> ORGANISM: Human

<400> SEQUENCE: 7

Lys Lys Gln Tyr Ile Lys Ala Asn Ser Lys Phe Ile Gly Ile Thr Glu
1               5                   10                  15

Leu Glu His Trp Ser Tyr Gly Leu Arg Pro Gly
            20                  25


<210> SEQ ID NO 8
<211> LENGTH: 45
<212> TYPE: PRT
<213> ORGANISM: Human

<400> SEQUENCE: 8

Thr Ala Lys Ser Lys Lys Phe Pro Ser Tyr Thr Ala Thr Tyr Gln Phe
1               5                   10                  15

Gly Gly Phe Phe Leu Leu Thr Arg Ile Leu Thr Ile Pro Gln Ser Leu
            20                  25                  30

Glu Gly Gly Glu His Trp Ser Tyr Gly Leu Arg Pro Gly
        35                  40                  45


<210> SEQ ID NO 9
<211> LENGTH: 45
<212> TYPE: PRT
<213> ORGANISM: Human

<400> SEQUENCE: 9

Thr Ala Lys Ser Lys Lys Phe Pro Ser Tyr Thr Ala Thr Tyr Gln Phe
1               5                   10                  15

Gly Gly Leu Ser Glu Ile Lys Gly Val Ile Val His Arg Leu Glu Gly
            20                  25                  30

Val Gly Gly Glu His Trp Ser Tyr Gly Leu Arg Pro Gly
        35                  40                  45


<210> SEQ ID NO 10
```

-continued

```
<211> LENGTH: 44
<212> TYPE: PRT
<213> ORGANISM: Human
<220> FEATURE:
<221> NAME/KEY: misc_feature
<222> LOCATION: (19)..(19)
<223> OTHER INFORMATION: Xaa indicates epsilon-Lys

<400> SEQUENCE: 10

Lys Lys Lys Ile Ile Thr Ile Thr Arg Ile Ile Thr Ile Ile Thr Thr
1               5                   10                  15

Ile Asp Xaa Cys Gly Glu Thr Tyr Gln Ser Arg Val Thr His Pro His
            20                  25                  30

Leu Pro Arg Ala Leu Met Arg Ser Thr Thr Lys Cys
        35                  40


<210> SEQ ID NO 11
<211> LENGTH: 45
<212> TYPE: PRT
<213> ORGANISM: Human
<220> FEATURE:
<221> NAME/KEY: misc_feature
<222> LOCATION: (20)..(20)
<223> OTHER INFORMATION: Xaa indicates epsilon-Lys

<400> SEQUENCE: 11

Ile Ser Ile Thr Glu Ile Lys Gly Val Ile Val His Arg Ile Glu Thr
1               5                   10                  15

Ile Leu Phe Xaa Cys Gly Glu Thr Tyr Gln Ser Arg Val Thr His Pro
            20                  25                  30

His Leu Pro Arg Ala Leu Met Arg Ser Thr Thr Lys Cys
        35                  40                  45
```